United States Patent [19]

Arakawa et al.

[11] Patent Number: 5,733,922

[45] Date of Patent: *Mar. 31, 1998

[54] IMIDAZOLE DERIVATIVE, PHARMACEUTICALLY ACCEPTABLE SALT THEREOF, AND ANTI-ULCER DRUG INCLUDING SUCH DERIVATIVE OR SALT

[75] Inventors: Eitaro Arakawa; Tetsuo Kato, both of Nagoya; Tsukasa Takamura, Toyota; Keiji Imai, Aichi-ken; Tetsuya Segami; Yukitaka Nakamura, both of Nagoya, all of Japan

[73] Assignee: Arax Co., Ltd., Japan

[ * ] Notice: The term of this patent shall not extend beyond the expiration date of Pat. No. 5,750,552.

[21] Appl. No.: 603,232

[22] Filed: Feb. 20, 1996

[30] Foreign Application Priority Data

Feb. 21, 1995 [JP] Japan ................... 7-032700

[51] Int. Cl.$^6$ ............... A61K 31/415; C07D 233/42
[52] U.S. Cl. ....................... 514/386; 548/320.1
[58] Field of Search ................ 548/320.1; 514/386

[56] References Cited

U.S. PATENT DOCUMENTS

| | | |
|---|---|---|
| 4,255,431 | 3/1981 | Junggren et al. . |
| 4,337,257 | 6/1982 | Junggren et al. . |
| 4,508,905 | 4/1985 | Junggren et al. . |

FOREIGN PATENT DOCUMENTS 0 354 788  2/1990  European Pat. Off. .

*Primary Examiner*—Patricia L. Morris

[57] ABSTRACT

An imidazole derivative represented by one of formulas (1), wherein $R_1$, $R_2$ represents hydrogen atom, lower alkyl, aryl, aralkyl group, or $R_1$ and $R_2$ cooperate to represent alkylene, alkylidene, arylalkylidene group, $R_3$ representing hydrogen atom, lower alkyl or alkanoyl group, or aralkyl or arylcarbonyl group, wherein at least one of A and B represents a group represented by formula (2), wherein m represents an integer 1-4, $R_4$ representing nitrogen-containing aromatic ring that may be substituted by lower alkyl, alkoxy or alkanoyl group, or phenyl group represented by formula (3), $R_5$, $R_6$ representing hydrogen atom, lower alkyl or alkenyl group, or lower alkanoyl or arylcarbonyl group which may be substituted by a halogen atom, $R_7$ representing hydrogen or halogen atom, hydroxyl or nitro group, or lower alkyl or alkoxy group, wherein the other of A and B represents oxygen or sulfur atom, hydroxyl, mercapto, alkylthio, alkenylthio or aralkylthio group, or group represented by the formula (2),

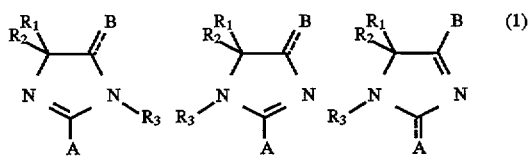

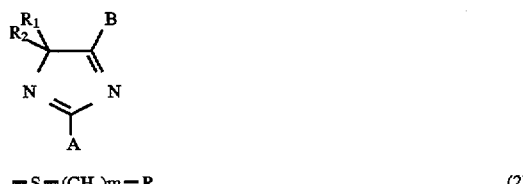

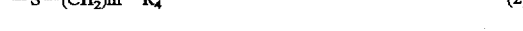

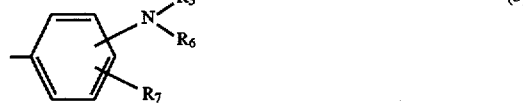

13 Claims, No Drawings

IMIDAZOLE DERIVATIVE, PHARMACEUTICALLY ACCEPTABLE SALT THEREOF, AND ANTI-ULCER DRUG INCLUDING SUCH DERIVATIVE OR SALT

BACKGROUND OF THE INVENTION

1. Field of the Invention

The present invention relates to novel imidazole derivatives, salts thereof pharmaceutically acceptable as a drug, a process suitable for producing the same, and an anti-ulcer drug including such an imidazole derivative or salt.

2. Discussion of the Prior Art

It is generally known that peptic ulcers such as gastric ulcer and duodenal ulcer are induced by imbalance between aggressive factors such as gastric acid and pepsin, and protective factors such as mucous, mucosal barrier and mucosal blood flow. Conventionally, therefore, various drugs for remedy of gastric ulcers have been used for inhibiting or suppressing the aggressive factors and/or promoting or intensifying the protective factors.

Typical examples of the aggressive factor inhibiting drugs that have been used are $H_2$-histamine receptor antagonists such as Cimetidine (Smith Kline & French Laboratories, United Kingdom) and Ranitidine (Glaxo, United Kingdom), and $H^+/K^+$ adenosine triphosphatase inhibitors (proton pump inhibitors) such as Omeprazole (Hassle, Sweden). However, such drugs have various problems, and do not exhibit a sufficient effect.

Described in detail, the $H_2$-histamine receptor antagonists provide an excellent effect to improve the symptoms of ulcer, but are likely to induce a recurrence of ulcer by a rebound of a dose thereof, undesirably requiring a continuous dosage thereof for a long period time. The proton pump inhibitors, on the other hand, is characterized by a relatively long effect, but has some potential drawbacks due to its tendency to cause anacidity in the stomach, for instance, proliferation of bacteria and an increase of N-nitroso compounds produced in the stomach, leading to clinically undesirable hypergastrinemia.

As the protective factor promoting drugs, there are known cetraxate, sofalcone and teprenone. However, these drugs are not satisfactory in their effects per dose, and their effects to improve the ulcer symptoms tend to be small. Therefore, their application is limited to concurrent use with the aggressive factor inhibiting drugs.

Thus, the anti-ulcer drugs currently available have the problems indicated above. The known aggressive factor inhibiting drugs and protective factor promoting drugs both suffer from unsatisfactory effects. In view of this prior art situation, there is a strong desire to develop an anti-ulcer drug which exhibits excellent effects of not only inhibiting the aggressive factors but also promoting the protective factors and which has a high degree of safety.

SUMMARY OF THE INVENTION

As a result of extensive research and study by the present inventors in an effort to solve the prior art problems, the inventors have found that some of compounds having an imidazole structure exhibit excellent effects of inhibiting the aggressive factors and promoting the protective factors and have a high degree of safety.

According to a first aspect of the present invention, there is provided an imidazole derivative or a pharmaceutically acceptable salt thereof, which is represented by one of the following formulas (44-1) through (44-4),

(44-1)

(44-2)

(44-3)

(44-4)

wherein $R_1$ and $R_2$ represent a same one or respective different ones of a hydrogen atom, a lower alkyl group, an aryl group that may have a substituent group, and an aralkyl group, or cooperate to represent one of an alkylene group, an alkylidene group and an arylalkylidene group that may have a substituent group, while $R_3$ represents one of a hydrogen atom, a lower alkyl group, an aralkyl group that may have a substituent group, a lower alkanoyl group and an arylcarbonyl group, and wherein at least one of A and X represents a group represented by the following formula (45),

$$-S-(CH_2)_m-R_4 \qquad (45)$$

wherein m represents one of integers "1" through "4", and $R_4$ represents a nitrogen-containing aromatic ring that may be substituted by one of a lower alkyl group, a lower alkoxy group and a lower alkanoyl group, or a phenyl group represented by the following formula (46),

(46)

wherein $R_5$ and $R_6$ represent a same one or respective different ones of a hydrogen atom, a lower alkyl group, a lower alkenyl group, and a lower alkanoyl or arylcarbonyl group which may be substituted by a halogen atom, while $R_7$ represents one of a hydrogen atom, a halogen atom, a hydroxyl group, a lower alkyl group, a lower alkoxy group and a nitro group, and wherein the other of A and X represents one of an oxygen atom, a sulfur atom, a hydroxyl group, a mercapto group, a group represented by the formula (45), an alkylthio group that may have a substituent group, alkenylthio group, and an aralkylthio group, and broken line in the formulas (44-1), (44-2) and (44-3)

represents a bond effective only when an appropriate one of A and X represents the oxygen or sulfur atom.

According to one preferred form of the above first aspect of this invention, $R_1$ and $R_2$ represent a same one or respective different ones of a hydrogen atom, an alkyl group having 1–7 carbon atoms and a phenyl group that may be a substituent group, or cooperate to represent one of an alkylidene group having 2–5 carbon atoms, a benzylidene or cinnamylidene group that may have a substituent group, and an alkylene group having 2–6 carbon atoms, and $R_3$ represents one of a hydrogen atom, an alkyl group having 1–7 carbon atoms, an alkanoyl group having 2–5 carbon atoms, an arylcarbonyl group, and a benzyl or cinnamyl group that may have a substituent group, and wherein at least one of A and X represents one of a group represented by the above-identified formula (45), while the other of said A and X represents one of an oxygen atom, a sulfur atom, a hydroxyl group, a mercapto group, an alkylthio group having 1–7 carbon atoms, an alkenylthio group, a benzylthio group that may have a substituent group, a cinnamylthio group, and a group represented by the formula (45). $R_4$ in the formula (45) represents one of an alkyl group having 1–4 carbon atoms, an alkoxy group, a pyridyl or quinolyl group that may be substituted by a phenylalkyl group that may have a substituent group, and a group represented by the formula (46), while $R_5$ and $R_6$ in the formula (46) represent a same one or respective different ones of a hydrogen atom, an alkyl group having 1–5 carbon atoms, an alkenyl group having 1–5 carbon atoms, an alkanoyl group of 1–5 carbon atoms or arylcarbonyl group that may be substituted by a halogen atom. $R_7$ in the formula (46) represents one of a hydrogen atom, a hydroxyl group, a halogen atom, an alkyl group having 1–5 carbon atoms, an alkoxy group having 1–5 carbon atoms and a nitro group.

According to a second aspect of this invention, the imidazole derivative or pharmaceutically acceptable salt thereof is represented by one of the following formulas (47-1), (47-2) and (47-3),

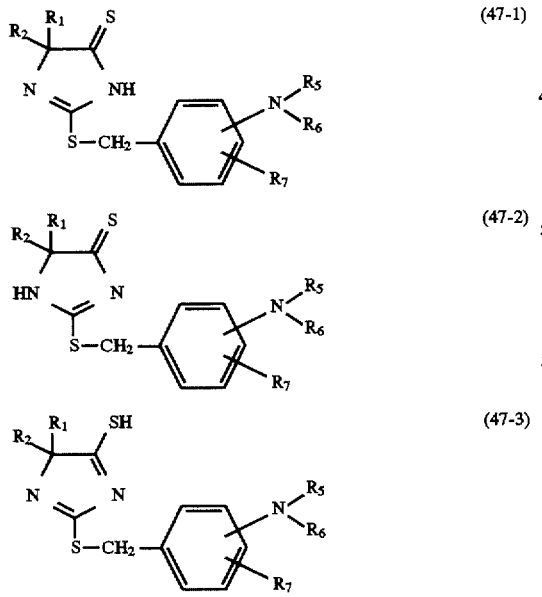

wherein $R_1$ and $R_2$ represent a same or respective ones of a hydrogen atom, an alkyl group having 1–7 carbon atoms, and a phenyl group that may have a substituent group, or cooperate to represent one of an alkylidene group having 2–5 carbon atoms, a benzylidene or cinnamylidene group that may have a substituent group, and an alkylene group having 2–6 carbon atoms, while $R_5$ and $R_6$ representing a same one or respective different ones of a hydrogen atom, an alkyl group having 1–5 carbon atoms, an alkenyl group having 1–5 carbon atoms, an alkanoyl group of 1–5 carbon atoms or arylcarbonyl group that may be substituted by a halogen atom. $R_7$ represents one of a hydrogen atom, a hydroxyl group, a halogen atom, an alkyl group having 1–5 carbon atoms an alkoxy group having 1–carbon atoms and a nitro group.

According to a third aspect of this present invention the imidazole derivative or pharmaceutically acceptable salt thereof, which is represented by the following formula (48),

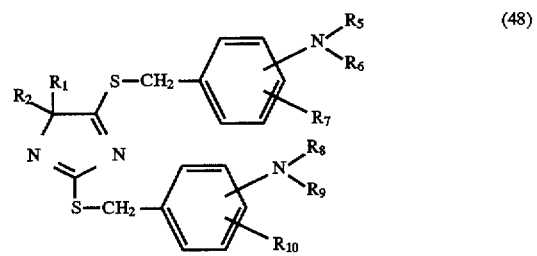

wherein $R_1$ and $R_2$ represent a same or respective ones of a hydrogen atom, an alkyl group having 1–7 carbon atoms, and a phenyl group that may have a substituent group, or cooperate to represent one of an alkylidene group having 2–5 carbon atoms, a benzylidene or cinnamylidene group that may have a substituent group, and an alkylene group having 2–6 carbon atoms, while $R_5$, $R_6$, $R_8$ and $R_9$ represent a same one or respective different ones of a hydrogen atom, an alkyl group having 1–5 carbon atoms, an alkenyl group having 1–5 carbon atoms, an alkanoyl group of 1–5 carbon atoms or arylcarbonyl group that may be substituted by a halogen atom, $R_7$ and $R_{10}$ representing any one of a hydrogen atom, a hydroxyl group, a halogen atom, an alkyl group having 1–5 carbon atom, an alkoxy group having 1–5 carbon atoms and a nitro group.

The imidazole derivative of the present invention as described above may be produced also according to the present invention, as described below.

In a first advantageous process according to a fourth aspect of this invention, the imidazole derivative which is represented by the following formula (49) is produced by effecting a reaction of a 2-thiohydantoin derivative represented by one of the following formulas (50-1), (50-2) and (50-3) with a compound represented by the following formula (51), and the pharmaceutically acceptable salt is produced by adding at least one acid as needed to the imidazole derivative,

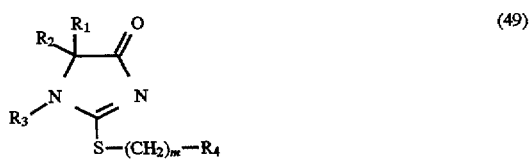

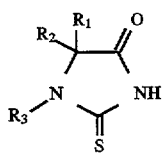 (50-1)

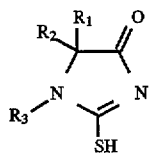 (50-2)

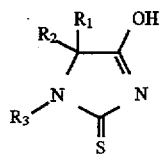 (50-3)

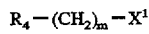

R$_4$—(CH$_2$)$_m$—X$^1$ (51)

wherein m represents one of integers "1" through "4", and R$_1$ and R$_2$ represent a same one or respective different ones of a hydrogen atom, a lower alkyl group, an aryl group that may have a substituent group, and an aralkyl group, or cooperate to represent one of an alkylene group, an alkylidene group or an arylalkylidene group that may have a substituent group, while R$_3$ represents one of a lower alkyl group, an aralkyl group that may have a substituent group, a lower alkanoyl group and an arylcarbonyl group, and wherein R$_4$ represents a nitrogen-containing aromatic ring that may be substituted by one of a lower alkyl group, an aralkyl group that may have a substituent group, a lower alkoxy group and a lower alkanoyl group, or a phenyl group represented by the above formula (46), and X$^1$ represents a halogen atom.

In a second advantageous process according to a fifth preferred aspect of this invention, pharmaceutically acceptable salt thereof, wherein the imidazole derivative which is represented by one of the following formulas (52-1), (52-2) and (52-3) is produced by effecting a reaction of a 2-thiohydantoin derivative represented by one of the following formulas (53-1) through (53-5) with a compound represented by the above-identified formula (51), and the pharmaceutically acceptable salt is produced by adding at least one acid as needed to the imidazole derivative,

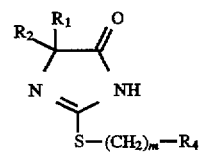 (52-1)

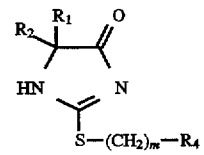 (52-2)

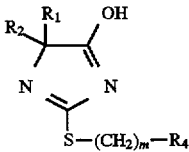 (52-3)

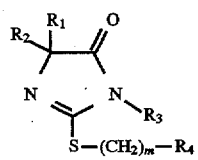 (53-1)

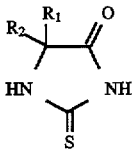 (52-2)

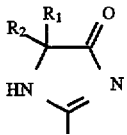 (53-3)

(53-4)

(53-5)

wherein R$_1$, R$_2$ and R$_4$ are the same as in the first advantageous process described above.

In a third advantageous process according to a sixth aspect of the invention, the imidazole derivative which is represented by the following formula (54) is produced by effecting a reaction of a compound represented by one of the above-identified formulas (52-1) through (52-3) with at least one of alkyl halide, aralkyl halide, acid halide and acid anhydride, and the pharmaceutically acceptable salt is produced by adding at least one acid as needed to the imidazole derivative,

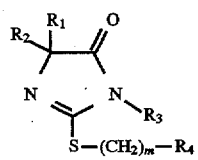 (54)

wherein R$_1$, R$_2$, R$_3$ and R$_4$ are the same as in the first advantageous process described above.

In a fourth advantageous process according to a seventh aspect of this invention, the imidazole derivative which is represented by the above-identified formula (54) is produced by effecting a reaction of a compound represented by one of the following formulas (55-1) and (55-2) with a compound represented by the above-identified formula (51), and the pharmaceutically acceptable salt is produced by adding at least one acid as needed to the imidazole derivative,

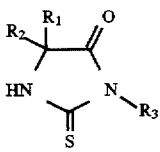 (55-1)

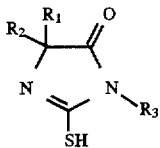 (55-2)

wherein $R_1$, $R_2$ and $R_3$ are the same as in the first advantageous process.

In a fifth advantageous process according to an eighth aspect of the present invention, the imidazole derivative which is represented by one of the following formulas (56-1), (56-2), (56-3), (57-1), (57-2) and (58) is produced by effecting a reaction of a 2,4-thiohydantoin derivative represented by one of the following formulas (59-1) through (59-5) with a compound represented by the above-identified formula (51), and the pharmaceutically acceptable salt is produced by adding at least one acid as needed to the imidazole derivative,

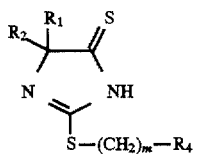 (56-1)

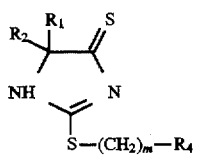 (56-2)

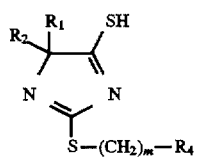 (56-3)

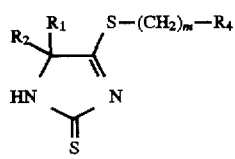 (57-1)

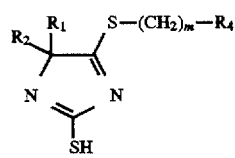 (57-2)

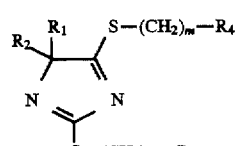 (58)

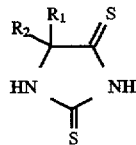 (59-1)

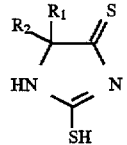 (59-2)

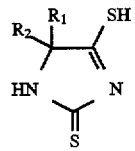 (59-3)

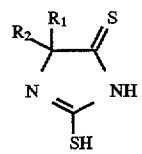 (59-4)

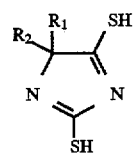 (59-5)

wherein $R_1$, $R_2$, $R_4$ and m are the same as in the first advantageous process described above.

In a fifth advantageous process according to one preferred form of the eighth aspect of the invention, "m" is equal to "1", and $R_4$ is a phenyl group represented by the formula (46).

In a sixth advantageous process according to a ninth aspect of this invention, the imidazole derivative which is represented by one of the following formulas (60) and (61) is produced by effecting a reaction of a compound represented by one of the above-identified formulas (56-1), (56-2), (56-3), (57-1) and (57-2) with a compound represented by the following formula (62), and the pharmaceutically acceptable salt is produced by adding at least one acid as needed to the imidazole derivative,

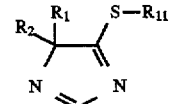 (60)

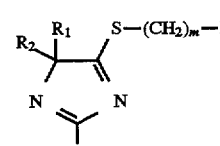 (61)

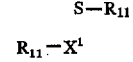 (62)

wherein $R_{11}$ represents one of an alkyl group having 1–7 carbon atoms, an alkenyl group having 3–5 carbon atoms, an aralkyl group that may have a substituent group, and a $R_{12}$—$(CH_2)_n$— group, and $R_{12}$ represents a nitrogen-containing aromatic ring that may be substituted by one of a hydrogen atom, a lower alkyl group, a lower alkoxy group and a lower alkanoyl group, or the phenyl group represented by the above formula (46). "X" represents a halogen atom.

In a sixth advantageous process according to the above ninth aspect of the invention, wherein "m" is equal to "1", and $R_4$ is the phenyl group represented by the above-identified formula (46), while $R_{11}$ is a group represented by the following formula (63),

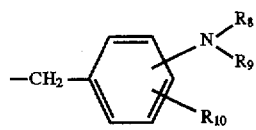
(63)

In a seventh advantageous process according to a tenth aspect of the invention, the imidazole derivative which is represented by one of the following formulas (64-1) and (64-2) is produced by effecting a reaction of a 4-thiohydantoin derivative represented by one of the following formulas (65-1) through (65-5) with a compound represented by the above-identified formula (51), and the pharmaceutically acceptable salt is produced by adding at least one acid as needed to the imidazole derivative,

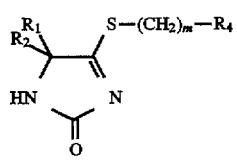
(64-1)

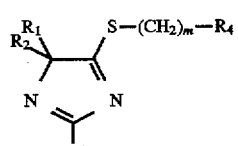
(64-2)

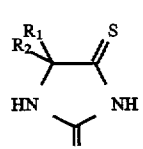
(65-1)

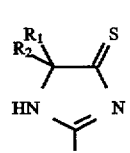
(65-2)

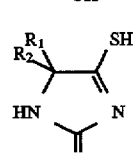
(65-3)

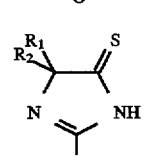
(65-4)

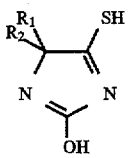
(65-5)

wherein $R_1$, $R_2$, $R_4$ and m are the same as in the first advantageous process described above.

In an eighth advantageous process according to the eleventh aspect of the present invention, the imidazole derivative which is represented by the following formula (66) is produced by effecting a reaction of a compound represented by one of the above-identified formulas (64-1) and (64-2) with at least one of alkyl halide, aralkyl halide, acid halide and acid anhydride, and said pharmaceutically acceptable salt is produced by adding at least one acid as needed to said imidazole derivative,

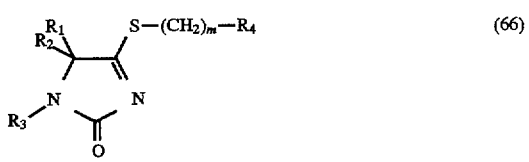
(66)

wherein $R_1$, $R_2$, $R_3$, $R_4$ and m are the same as in the first advantageous process described above.

It is noted that the alkyl groups or alkyl group portions of their substituents in the structural formulas (44) through (66) indicated above may be either linear or branched.

According to a twelfth aspect of this invention, there is provided an anti-ulcer drug including as an effective component a novel imidazole derivative or pharmaceutically acceptable salt thereof, which derivative is represented by the above formula (46), for example.

DETAILED DESCRIPTION OF THE INVENTION

In the formulas (44-1) through (44-4), $R_1$ and $R_2$ represent the same or respective different ones of a hydrogen atom, a linear or branched lower alkyl group, a phenyl group, a benzyl group and a p-hydroxybenzyl group, for example. The lower alkyl group may be a methyl group, an ethyl group, a propyl group, a butyl group, an isopropyl group or an isobutyl group. Alternatively, $R_1$ and $R_2$ cooperate to represent one of a methylidene group, an ethylidene group, a propylidene group, an isopropylidene group, a benzylidene group, a cinnamylidene group, a trimethylene group, a tetramethylene group, a pentamethylene group and a hexamethylene group.

$R_3$ may be selected from among a hydrogen atom, a linear or branched lower alkyl group, a benzyl group, a cinnamyl group, an acetyl group and a benzoyl group. The lower alkyl group may be selected from among methyl, ethyl, propyl, butyl isopropyl and isobutyl groups.

In the formulas (44), at least one of A and B represent a group represented by the above-formula (45), while the other of A and B represents one of an oxygen atom, a sulfur atom, a hydroxyl group, a mercapto group, a methylthio group, an ethylthio group, a propylthio group, a butylthio group, an isopropylthio group, an isobutylthio group, an allylthio group, a benzylthio group, a cinnamylthio group, and a group represented by the above formula (45).

$R_4$ in the above formula (45) may represent one of a 2-dimethylaminophenyl group, a 3-dimethylaminophenyl group, a 4-dimethylaminophenyl group, a 2-dimethylamino- 4-fluorophenyl group, a 2-dimethylamino-5-fluorophenyl group, a 2-dimethylamino-3-chlorophenyl group, a 2-dimethylamino-4-chlorophenyl group, a 2-dimethylamono-5-chlorophenyl group, a 2-dimethylamino-6-chlorophenyl group, a 2-dimethylamino-5-bromophenyl group, a 2-dimethylamino-3-methylphenyl group, a 2-dimethylamino-4-methylphenyl group, a 2-dimethylamino-5-methylphenyl group, a 2-dimethylamino-6-methylphenyl group, a 2-dimethylamino-4-nitrophenyl group, a 2-dimethylamino-5-nitrophenyl group, a 5-hydroxy-2-dimethylaminophenyl group, a 2-dimethylamino-3-methoxylphenyl group, a 2-dimethylamino-5-methoxyphenyl group, a 2-dimethylamino-4,5-dimethoxylphenyl group, a 2-N-ethyl-N-methylaminophenyl group, a 3-N-ethyl-N-methylaminophenyl group, a 4-N-ethyl-N-methylaminophenyl group, a 2-diethylaminophenyl group, a 3-diethylaminophenyl group, a 4-diethylaminophenyl group, a 2-N-isobutyl-N-methylaminophenyl group, a 3-N-isobutyl-N-methylaminophenyl group, a 4-N-isobutyl-N-methylaminophenyl group, a 2-N-trifluoroethyl-N-methylaminophenyl group, a 2-N-aryl-N-methylaminophenyl group, a 2-methylaminophenyl group, a 3-methylaminophenyl group, a 4-methylaminophenyl group, a 2-N-trifluoroethylaminophenyl group, a 2-aminophenyl group, a 3-aminophenyl group, a 4-aminophenyl group, a 2-N-acetylaminophenyl group, a 3-N-acetylaminophenyl group, a 4-N-acetylaminophenyl group, a 2-N-formyl-N-methylaminophenyl group, a 2-N-formylaminophenyl group, a 2-N-trifluoroacetylaminophenyl group, a 3-N-trifluoroacetylaminophenyl group, a 4-N-trifluoroacetylaminophenyl group, a 2-pyridyl group, a 3-pyridyl group, a 4-pyridyl group, a 4-methoxy-2-pyridyl group, a 3,5-dimethyl-2-pyridyl group, a 3,4,5-trimethyl-2-pyridyl group, a 4-methoxy-5-methyl-2-pyridyl group, a 4-methoxy-3,5-dimethyl-2-pyridyl group, a 2-quinolinyl group and a 8-quinolinyl group.

Examples of the imidazole derivative represented by the above formulas (44-1) through (44-4) include the following:
(1) 2-(2-pyridylmethylthio)imidazolin-4-one
(2) 2-(2-dimethylaminobenzylthio)imidazolin-4-one
(3) 2-(4-methoxy-3,5-dimethyl-2-pyridylmethylthio)-5-trans-benzylideneimidazolin-4-one
(4) 2-(4-methoxy-3,5-dimethyl-2-pyridylmethylthio) imidazolin-4-one
(5) 2-(2-pyridylmethylthio)-5-trans-benzylideneimidazolin-4-one
(6) 2-(2-pyridylmethylthio)-5-trans-methylideneimidazolin-4-one
(7) 2-(2-dimethylaminobenzylthio)-5-transbenzylideneimidazolin-4-one
(8) 2-(2-dimethylaminobenzylthio)-trans-methylideneimidazolin-4-one
(9) 2-(4-methoxy-3,5-dimethyl-2-pyridylmethylthio)-5-trans-methylideneimidazolin-4-one
(10) 2-(2-N-isobutyl-N-methylaminobenzylthio)imidazolin-4-one
(11) 2-(2-pyridylmethylthio)-5,5-diphenylimidazolin-4-one
(12) DL-2-(2-pyridylmethylthio)-5-benzylimidazolin-4-one
(13) DL-2-(2-dimethylaminobenzylthio)-5-benzylimidazolin-4-one
(14) 2-(2-pyridylmethylthio)-5,5-dimethylimidazolin-4-one
(15) 2-(2-dimethylaminobenzylthio)-5,5-dimethylimidazolin-4-one
(16) 2-(2-N-isobutyl-N-methylaminobenzylthio)-5,5-dimethylimidazolin-4-one
(17) DL-2-(2-dimethylaminobenzylthio)-5-methylimidazolin-4-one
(18) DL-2-(2-pyridylmethylthio)-5-methylimidazolin-4-one
(19) 2-(2-pyridylmethylthio)-5-phenyl-5-methylimidazolin-4-one
(20) 2-(2-dimethylaminobenzylthio)-5-phenyl-5-methylimidazolin-4-one
(21) 2-(2-dimethylaminobenzylthio)-5-ethyl-5-methylimidazolin-4-one
(22) 2-(2-pyridylmethylthio)-5,5-dipropylimidazolin-4-one
(23) 2-(2-dimethylaminobenzylthio)-5,5-dipropylimidazolin-4-one
(24) 2-(2-pyridylmethylthio)-5-phenyl-5-ethylimidazolin-4-one
(25) 2-(2-dimethylaminobenzylthio)-5-phenyl-5-ethylimidazolin-4-one
(26) 2-(2-dimethylaminobenzylthio)-5,5-diethylimidazolin-4-one
(27) 2-(2-dimethylaminobenzylthio)-5-butyl-5-ethylimidazolin-4-one
(28) 2-(2-dimethylaminobenzylthio)-5-isobutyl-5-methylimidazolin-4-one
(29) 2-(2-pyridylmethylthio)-5-butyl-5-ethylimidazolin-4-one
(30) 2-(2-pyridylmethylthio)-5-isobutyl-5-methylimidazolin-4-one
(31) 1-N-acetyl-2-(2-dimethylaminobenzylthio)-5,5-dimethyl-2-imidazolin-4-one
(32) 1-N-acetyl-2-(2-dimethylaminobenzylthio)-5,5-diethyl-2-imidazolin-4-one
(33) 1-N-acetyl-2-(2-dimethylaminobenzylthio)-4,4-dimethyl-2-imidazolin-4-one
(34) 2-(2-dimethylaminobenzylthio)-5,5-dimethylimidazolin-4-thione
(35) 2-(2-dimethylaminobenzylthio)-5,5-diethylimidazolin-4-thione
(36) 2,4-bis-(2-dimethylaminobenzylthio)-5,5-diethyl-5H-imidazole
(37) 2-(2-dimethylaminobenzylthio)-5-phenyl-5-methylimidazolin-4-thione
(38) 2,4-bis(2-dimethylaminobenzylthio)-5-phenyl-5-methyl-5H-imidazole
(39) 2-(2-dimethylaminobenzylthio)-5-ethyl-5-methylimidazolin-4-thione
(40) 2,4-bis(2-dimethylaminobenzylthio)-5-ethyl-5-methyl-5H-imidazole
(41) 4-benzylthio-2-(2-dimethylaminobenzylthio)-5,5-dimethyl-5H-imidazole
(42) 4-(2-dimethylaminobenzylthio)-5,5-dimethyl-3-imidazolin-2-one
(43) 4-(2-dimethylaminobenzylthio)-5-ethyl-5-methyl-3-imidazolin-2-one
(44) 2-benzylthio-4-(2-dimethylaminobenzylthio)-5,5-dimethyl-5H-imidazole
(45) 2,4-bis(2-dimethylaminobenzylthio)-5,5-dimethyl-5H-imidazole
(46) 2-(2-N-isobutyl-N-methylaminobenzylthio)-5,5-dimethylimidazolin-4-thione
(47) 2,4-bis(2-N-isobutyl-N-methylaminobenzylthio)-5,5-dimethyl-5H-imidazole
(48) 2,4-bis(2-pyridylmethylthio)-5,5-dimethyl-5H-imidazole
(49) 2,4-bis(4-dimethylaminobenzylthio)-5,5-dimethyl-5H-imidazole
(50) 4-(2-N-acetylaminobenzylthio)-5,5-dimethylimidazolin-2-thione
(51) 2,4-bis(2-N-acetylaminobenzylthio)-5,5-dimethyl-5H-imidazole

(52) 2-(2-N-formyl-N-methylaminobenzylthio)-5,5-dimethylimidazolin-4-thione
(53) 4-(2-quinolinylmethylthio)-5,5-dimethylimidazolin-2-thione
(54) 2-(8-quinolinylmethylthio)-5,5-dimethylimidazolin-2-thione
(55) 1-N-methyl-4-(2-dimethylaminobenzylthio)-5,5-dimethyl-3-imidazolin-2-one
(56) 4-(2-dimethylaminobenzylthio)-5,5-dimethylimidazolin-2-thione
(57) 2-(3-dimethylaminobenzylthio)-5,5-dimethylimidazolin-4-thione
(58) 4-(3-dimethylaminobenzylthio)-5,5-dimethylimidazolin-2thione
(59) 2,4-bis(8-quinolinylmethylthio)-5,5-dimethyl-5H-imidazole
(60) 2,4-bis(3-dimethylaminobenzylthio)-5,5-dimethyl-5H-imidazole
(61) 2-(2-N-benzoylaminobenzylthio)-5,5-dimethylimidazolin-4-thione
(62) 4-(2-N-benzoylaminobenzylthio)-5,5-dimethylimidazolin-2-thione
(63) 2,4-bis(2-N-benzoylaminobenzylthio)-5,5-dimethyl-5H-imidazole
(64) 2-(2-N-ethyl-N-methylaminobenzylthio)-5,5-dimethylimidazolin-4-thione
(65) 2,4-bis(2-N-ethyl-N-methylaminobenzylthio)-5,5-dimethyl-5H-imidazole
(66) 2-(2-pyridylmethylthio)-5,5-dimethylimidazolin-4-thione
(67) 2,4-bis(2-quinolinylmethylthio)-5,5-dimethyl-5H-imidazole
(68) 1-N-methyl-2-(2-dimethylaminobenzylthio)-4,4-dimethyl-2-imidazolin-5-thione
(69) 2-(2-N-trifluoroacetylaminobenzylthio)-5,5-dimethylimidazolin-4-thione
(70) 2-4-bis(2-N-trifluoroacetylaminobenzylthio)-5,5-dimethyl-5H-imidazole
(71) 2-(2-aminobenzylthio)-5,5-dimethylimidazolin-4-thione
(72) 2-(2-N-methylaminobenzylthio)-5,5-dimethylimidazolin-4-thione
(73) 2-(2-dimethylamino-5-methylbenzylthio)-5,5-dimethylimidazolin-4-thione
(74) 2,4-bis(2-dimethylamino-5-methylbenzylthio)-5,5-dimethyl-5H-imidazole
(75) 2-(2-dimethylamino-3-methylbenzylthio)-5,5-dimethylimidazolin-4-thione
(76) 2,4-bis(2-dimethylamino-3-methylbenzylthio)-5,5-dimethyl-5H-imidazole
(77) 2-(2-dimethylamino-5-hydroxybenzylthio)-5,5-dimethylimidazolin-4-thione
(78) 2,4-bis(2-dimethylamino-5-hydroxybenzylthio)-5,5-dimethyl-5H-imidazole
(79) 2-(2-N-trifluoroacetyl-N-methylaminobenzylthio)-5,5-dimethylimidazolin-4-thione
(80) 2,4-bis(2-N-trifluoroacetyl-N-methylaminobenzylthio)-5,5-dimethyl-5H-imidazole
(81) 2-(5-chloro-2-dimethylaminobenzylthio)-5,5-dimethylimidazolin-4-thione
(82) 2,4-bis(5-chloro-2-dimethylaminobenzylthio)-5,5-dimethyl-5H-imidazole
(83) 2-(4-chloro-2-dimethylaminobenzylthio)-5,5-dimethylimidazolin-4-thione
(84) 2,4-bis(4-chloro-2-dimethylaminobenzylthio)-5,5-dimethyl-5H-imidazole
(85) 2-(2-dimethylamino-5-methoxybenzylthio)-5,5-dimethylimidazolin-4-thione
(86) 2,4-bis(2-dimethylamino-5-methoxybenzylthio)-5,5-dimethyl-5H-imidazole
(87) 2-(2-methylaminobenzylthio)-5,5-dimethylimidazolin-4-thione
(88) 2,4-bis(2-methylaminobenzylthio)-5,5-dimethyl-5H-imidazole
(89) 2-(2-dimethylamino-4-fluorobenzylthio)-5,5-dimethylimidazolin-4-thione
(90) 2,4-bis(2-dimethylamino-4-fluorobenzylthio)-5,5-dimethyl-5H-imidazole
(91) 2-(2-dimethylamino-4-nitrobenzylthio)-5,5-dimethylimidazolin-4-thione
(92) 2,4-bis(2-dimethylamino-4-nitrobenzylthio)-5,5-dimethyl-5H-imidazole
(93) 2-(2-dimethylamino-5-nitrobenzylthio)-5,5-dimethylimidazolin-4-thione
(94) 2,4-bis(2-dimethylamino-5-nitrobenzylthio)-5,5-dimethyl-5H-imidazole
(95) 2-[2-N-(2,2,2-trifluoroethyl)-N-methylaminobenzylthio]-5,5-dimethylimidazolin-4-thione
(96) 2,4-bis[2-N-(2,2,2-trifluoroethyl)-N-methylaminobenzylthio]-5,5-dimethyl-5H-imidazole
(97) 2-(2-N-aryl-N-methylaminobenzylthio)-5,5-dimethylimidazolin-4-thione
(98) 2-[2-N-(2,2,2-trifluoroethyl)aminobenzylthio]-5,5-dimethylimidazolin-4-thione
(99) 2,4-bis[2-N-(2,2,2-trifluoroethyl)aminobenzylthio]-5,5-dimethyl-5H-imidazole
(100) 2-(2-N-formylaminobenzylthio)-5,5-dimethylimidazolin-4-thione
(101) 2-(2-N-acetylaminobenzylthio)-5,5-dimethylimidazolin-4-thione By inducing a reaction of the imidazole derivatives as described above with a suitable acid, salts that are pharmaceutically acceptable as drugs may be obtained. For example, the acid used for this purpose may be selected from among: inorganic acids, such as hydrochloric acid, hydrobromic acid, phosphoric acid and sulfuric acid; and organic acids, such as acetic acid, citric acid, succinic acid, tartaric acid, fumaric acid, maleic acid, methane sulfonic acid and p-toluenesulfonic acid.

Compounds which are represented by the above formulas (44) and in which A or B is an oxygen atom may be prepared according to reactions (a) through (f) as indicated in the following formula (67) wherein $R_1, R_2, R_3, R_4$ and m are the same as in the above formulas (44) through (46), and $X^1$ represents a halogen atom.

Described in detail, a desired compound (III) is obtained by the reaction (a) between compounds (I) and (II), while a desired compound (V) is obtained by the reaction (b) between the compound (II) and a compound (IV). A compound (VI) is obtained by the reaction (c) between the compound (V) and alkyl halide, aralkyl halide, acid halide or acid anhydride. The compound (VI) may be obtained also by the reaction (d) between a compound (VII) and the compound (II).

Further, a compound (IX) is obtained by the reaction (e) between a compound (VIII) and the compound (II). Like the reaction (c), the reaction (f) of the thus obtained compound (IX) with alkyl, aralkyl or acid halide or acid anhydride produces a compound (X).

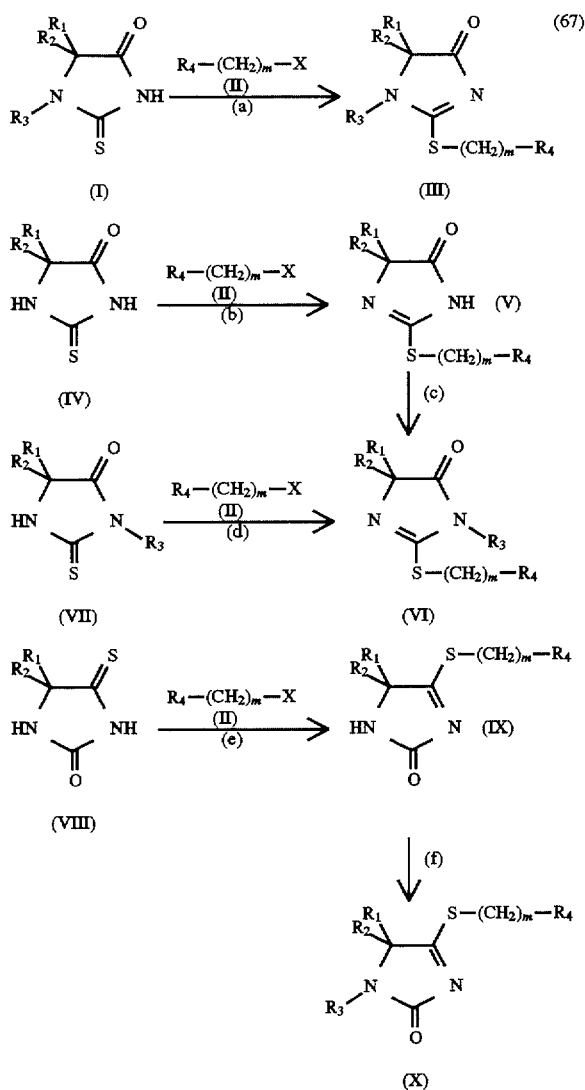

Explained more specifically, the compounds (I), (IV), (VII) and (VIII) as starting materials used for the reactions (a), (b), (d) and (e) are generally commercially available, or may be prepared by processes described in: Yakugaku Zasshi, Vol. 8, pp 30, 1960;Yakugaku Zasshi, vol. 18, p 37, 1970; Journal of American Chemical Society (J. Am. Chem. Soc.), Vol. 33, pp 1973, 1911; Chemische Berichte, Vol. 95, pp 2885, 1962; Journal of Chemical Society, pp 396, 1959; and Bulletin de la Société Chemique de France, pp 228, 1949.

The compound (II) used in the above reactions (a), (b), (d) and (e) may take the form of a salt, and is generally used in an equivalent amount of 1.–5, preferably 1–1.5.

Those reactions (a), (b), (d) and (e) may take place in the presence of an acid receptor, which may be selected from the group consisting of: alkaline metal compounds such as sodium hydrogencarbonate, sodium carbonate, potassium carbonate, sodium hydroxide and sodium methoxide; and organic tertiary amines such as pyridine, trimethylamine, triethylamine, diisopropylethylamine, and 4-dimethylaminopyridine. Such acid receptor is used in an equivalent amount of 1–6 with respect to the compound (I), (IV), (VII) or (VIII).

The reactions are generally effected at a temperature within a range between −30° C. and 150° C., preferably between 0° C. and 120° C., and more preferably 0° C. and 80° C. A solvent for the reactions may be selected from the group consisting of: alkanols such as methanol and ethanol; hydrocarbon halides such as dichloromethane and chloroform; aromatic compounds such as benzene, toluene and pyridine; acetonitrile; dimethylformamide; and dimethylsulfoxide.

Where alkylation is effected in the reaction (c) or (f), alkyl halide or aralkyl halide is generally used in an equivalent amount of 1–10 with respect to the compound (V) or (IX). The reaction may take place in the presence of an acid receptor. In this case, the acid receptor may be selected from the group consisting of: sodium hydrogencarbonate; sodium carbonate; potassium carbonate; sodium hydroxide; triethylamine; diisopropylethylamine; and 4-dimethylaminopyridine. The reaction solvent may be selected from among tetrahydrofuran, dioxane, acetonitrile, dimethylformamide, dimethylsulfoxide and hydrocarbon halide. The reaction temperature is generally within a range of 0°–80° C.

Where acylation is effected in the reaction (c) or (f), on the other hand, an equivalent amount of 1–100 of acid anhydride or 1–10 of acid halide is generally used with respect to the compound (V) or (IX). Where acid anhydride is used, it may be dissolved in a suitable solvent. In this case, pyridine is generally used as the solvent. Where acid halide is used, the reaction may take place in the presence of an acid receptor, which may be generally selected from among sodium carbonate, potassium carbonate, sodium hydroxide, triethylamine, diisopylethylamine, and 4-dimethylaminopyridine. The reaction solvent may be selected from among tetrahydrofuran, dioxane, acetonitrile, dimethylformamide, dimethylsulfoxide, hydrocarbon halide, benzene, toluene and pyridine. The reaction temperature is generally within a range of 0°–150° C.

Compounds which are represented by the above formulas (44) and in which none of A and B is an oxygen atom may be prepared in a process according to the following formula (68).

In the above formula (68), m, $R_1$, $R_2$, $R_3$ and $R_4$ are the same as in the above formulas (44) through (46), and $X^1$ represents a halogen atom. $R_{11}$ represents one of an alkyl group having 1–7 carbon atoms, an alkenyl group having 3–5 carbon atoms, an aralkyl group that may have a substituent group, and a $R_{12}$—$(CH_2)_n$— group, where $R_{12}$ represents a nitrogen-containing aromatic ring that may be substituted by one of a hydrogen atom, a lower alkyl group, a lower alkoxy group and a lower alkanoyl group, or represents a phenyl group represented by the above formula (46), and "n" represents an integer of 1–4.

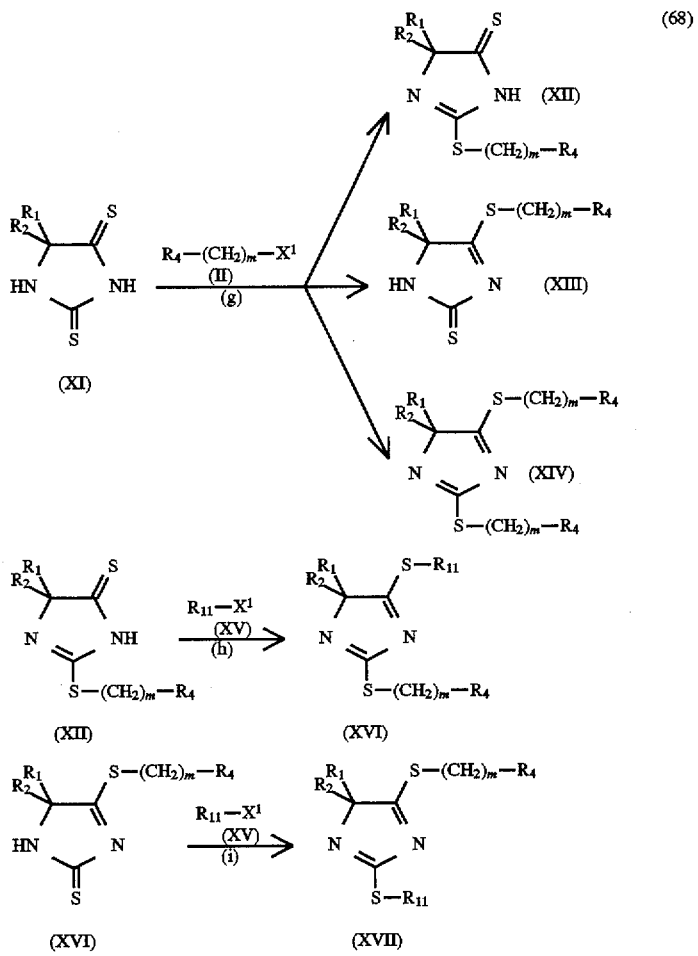

(68)

In the process according to the above formula (68), compounds (XII), (XIII) and (XIV) are obtained by a reaction (g) between a compound (XI) and the compound (II). In the reaction (g), the compound (II) may take the form of a salt, and is generally used in an equivalent amount of 1–5, preferably 1–1.5 with respect to the compound (XI). For obtaining primarily the compound (XII) or (XIII), the compound (II) is used preferably in an equivalent amount of 1–1.5, more preferably 1–1.1. For obtaining primarily the compound (XIV), the compound (II) is used preferably in an equivalent amount of 2–5, more preferably 2–3 with respect to the compound (XI). The reaction temperature is generally held within a range between –30° C. and 150° C., preferably between –20° C. and 120° C., more preferably –20° C. and 80° C. The reaction solvent may be selected from among: alkanols such as methanol and ethanol; hydrocarbon halides such as dichloromethane and chloroform; aromatic compounds such as benzene, toluene and pyridine; acetonitrile; dimethylformamide; and dimethylsulfoxide.

The compound (XI) used as a starting material in the reaction (g) may be prepared in various known processes, for example, processes as described in: Chemische Berichte, Vol. 95, pp 2885, 1962; Acta Chimica Academiae Scientiarum Hungaricae, Vol. 51, pp 95, 1967; Acta Chimica Academiae Scientiarum Hungaricae, Vol. 50, pp 303, 1966; Journal of Chemical Society, pp 354, 1950.

A compound (XVI) is obtained by a reaction (h) between the compound (XII) obtained by the reaction (g) and a compound (XV). Further, a compound (XVII) is obtained by a reaction (i) between the compound (XIII) obtained by the reaction (g) and a compound (XV). The compound (XV) is used generally in an equivalent amount of 1–5, preferably 1–2, with respect to the compound (XII) or (XIII). The reaction solvent may be selected from among tetrahydrofuran, dioxane, acetonitrile, dimethylformamide, dimethylsulfoxide, and hydrocarbon halides. The reaction temperature is in a range of 0°–80° C.

The reactions (g) through (i) may take place in the presence of an acid receptor, which may be selected from the group consisting of: alkali metal compounds such as sodium hydrogencarbonate, sodium carbonate, potassium carbonate, sodium hydroxide and sodium methoxide; and organic tertiary amines such as pyridine, trimethylamine, triethylamine, diisopropylethylamine, and 4-dimethylaminopyridine.

While the processes of producing the novel imidazole derivatives according to the present invention have been described above, these derivatives are extracted and purified by crystallization or column chromatography from the reaction mixtures.

The thus purified imidazole derivatives may be processed into salts pharmaceutically acceptable as drugs, by inducing a reaction of the imidazole derivatives with suitable acids, for example, inorganic acids such as hydrochloric acid, hydrobromic acid, phosphoric acid and sulfuric acid, or organic acids such as acetic acid, citric acid, succinic acid, tartaric acid, fumaric acid, maleic acid, methane sulfonic acid and p-toluenesulfonic acid.

The compounds (I), (IV), (V), (VII), (VIII), (IX), (XI), (XII) and (XIII) produced by the reactions according to the above formulas (67) and (68) contain tautomers. The reactions of these tautomers to obtain the desired starting compounds or final compounds are effected in substantially the same manner as described above in detail. These reactions are considered to be a part of the process of producing the imidazole derivatives according to the principle of the present invention.

Those tautomers are illustrated in the following formulas (69) through (77). The formulas (69-1), (69-2) and (69-3) indicate the tautomers of the compound (I). The formulas (70-1) through (70-5) indicate the tautomers of the compound (IV). The formulas (71-1) through (71-3) indicate the tautomers of the compound (V). The formulas (72-1) and (72-2) indicate the tautomers of the compound (VII). The formulas (73-1) through (73-5) indicate the tautomers of the compound (VIII). The formulas (74-1) and (74-2) indicate the tautomers of the compound (IX). The formulas (75-1) through (75-5) indicate the tautomers of the compound (XI). The formulas (76-1) through (76-3) indicate the tautomers of the compound (XII), and the formulas (77-1) and (77-2) indicate the tautomers of the compound (XIII).

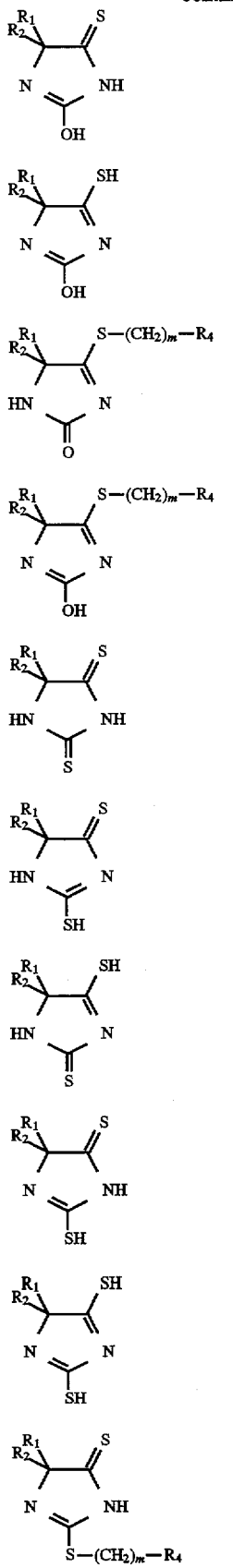

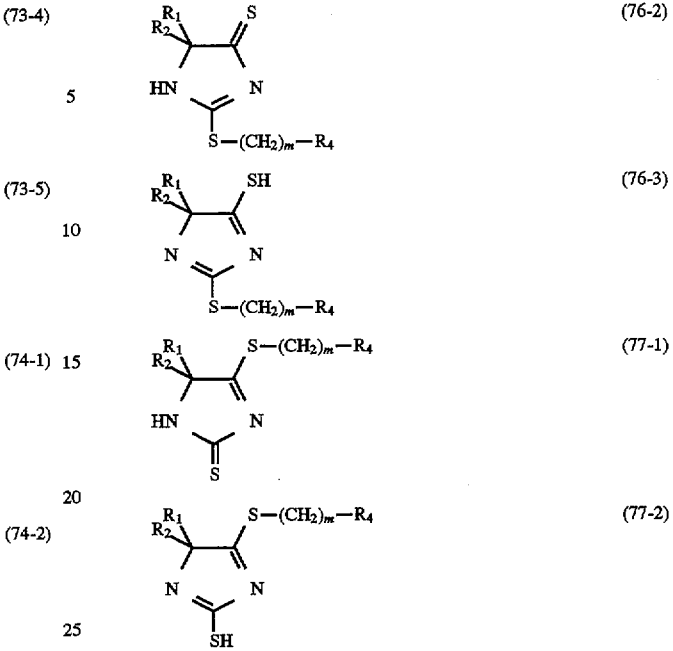

The tautomers of the imidazole derivatives produced according to this invention have respective stable structures. For example, X-ray crystal structure analysis of 2-(2-dimethylaminobenzylthio)-5,5-dimethylimidazolin-4-thione which was prepared in Example 39 (which will be described) by the above-explained reaction (g) took the form of 2-(2-dimethylaminobenzylthio)-4,4-dimethyl-2-imidazolin-5-thione in its crystalline state.

The compounds represented by the above formulas (44) according to the present invention, and their salts which are pharmaceutically acceptable as drugs have effects to inhibit or suppress the aggressive factors for peptic ulcers and promote or intensify the protective factors for the peptic ulcers. Thus, the nobel imidazole derivatives according to the present invention may act as an effective component of an anti-ulcer drug also according to the present invention. The anti-ulcer drug is formulated in an ordinary process.

Described in detail, the anti-ulcer drug according to the present invention contains, as an effective component, an imidazole derivative of the present invention or a pharmaceutically acceptable salt thereof, and also contains suitable additives as needed, such as a binder, an excipien or vehicle, a lubricant, an emulsifier, a disintegrater, a wetting agent, an antiseptics, and a coloring agent, which are used for pharmaceuticals general. The binder may be selected from among gum arabic, polyvinylpyrrolidone, sorbit, tragacanth and gelatin. The excipien may be selected from among lactose, sugar, sorbit, Corn starch, calcium phosphate and glycine. The lubricant may be selected from among magnesium stearate, talc, polyethylene glycol and silica. The disintegrator may be selected from among carboxymethyl cellulose calcium and Potato starch. The wetting agent may be selected from among methyl cellulose, aluminum stearate gel, carboxymethyl cellulose, gelatin, hydroxyethyl cellulose, hydrogenated edible oil and sorbit syrup. The antiseptics may be sorbic acid or p-hydroxybenzoic acid.

The anti-ulcer drug of the present invention may take various known forms such as tablets, powder, granule, capsules, solution, and parenteral injection. The dose of the anti-ulcer drug should be suitably adjusted depending upon the age, weight and ulcer symptom of the patient and the type of administration of the drug. In the case of oral administration, a suitable dose of the anti-ulcer drug for an ordinary adult per day is such that the amount of the imidazole derivative or its pharmaceutically acceptable salt as the effective component of the drug is about 1–1000 mg.

There will be described some examples of the present invention to further clarify the concept of this invention. It is to be understood that the present invention is not limited to the details of these examples.

EXAMPLE 1

Preparation of 2-(2-pyridylmethylthio)imidazolin-4-one

Initially, 1 g of 2-thiohydantoin and 2.5 g of sodium methylate were dissolved in 50 mL of methanol (MeoH), and 1.5 g of 2-chloromethylpyridine hydrochloride was added to the solution. The reaction mixture was stirred under reflux for one and a half hour and concentrated in vacuo. To the residue, there was added 50 mL of chloroform ($CHCl_3$), and the mixture was washed with 50 mL of water. Then, the $CHCL_3$ layer was dried over magnesium sulfate ($MgSO_4$) and concentrated in vacuo. The residue was purified by column chromatography [using a developing solvent consisting of $CHCl_3$:MeOH=50:1 (volume ratio, v/v)]. Recrystallization from diethylether gave the desired compound in the form of a needle-like crystal. The yield of this compound was 1.2 g with a yield ratio of 67.2%, and its melting point was 105°–107° C.

A result of a $^1$H-NMR analysis of this compound is as follows:

$^1$H-NMR ($CDCl_3$, δ, ppm, TMS) 4.13(2H, s, C—$CH_2$—N), 4.45 (2H, s, —$CH_2$—Ar), 7.13~8.73 (4H, m, Ar)

EXAMPLE 2

Preparation of 2-(4-methoxy-3,5-dimethyl-2-pyridylmethylthio)-5-trans-benzylideneimidazolin-4-one initially, 1.7 g of 5-trans-benzylidene-2-thiohydantoin and 1.9 g of sodiummethylate were dissolved in 50 mL of methanol (MeOH), and 2.1 g of 2-chloromethyl-4-methoxy-3,5- dimethylpyridine hydrochloride was added to the solution. The reaction mixture was stirred for one hour under reflux and concentrated in vacuo. To the thus obtained residue, there was added 100 mL of water. The precipitate was then filtered and crystallized from MeOH—$CHCl_3$ to give the desired compound in the form of needle-like crystal. The yield of this compound was 1.75 g, with a yield ratio of 59.5%, and its melting point was 239°–242° C.

A result of a $^1$H-NMR analysis of the compound is as follows:

$^1$H-NMR ($CDCl_3$+DMSO-$d_6$, δ, ppm, TMS) 2.23, 2.35 (6H, each s, Ar —$CH_3$×2), 3.77 (3H, s, —$OCH_3$), 4.74 (2H, s, —$CH_2$—Ar), 6.76 (1H, s, =CH—Ar), 7.36~8.34 (6H, m, Ar)

In the following Examples 3–15, desired compounds were prepared using appropriate starting compounds, in the same manner as in Example 1. The yield ratio, melting point and $^1$H-NMR analysis result of each of these compounds are indicated below.

EXAMPLE 3

Preparation of 2-(4-methoxy-3,5-dimethyl-2-pyridylmethylthio)imidazolin-4-one

Yield ratio: 70.0% Melting point: 157°–160° C.

$^1$H-NMR ($CDCl_3$+DMSO-$d_6$, δ, ppm, TMS) 2.24 (3H, s, Ar—$CH_3$), 2.27 (3H, s, Ar—$CH_3$), 3.72 (3H, s, —$OCH_3$), 4.05 (2H, s, C—$CH_2$—N), 4.62 (2H, s, —$CH_2$—Ar), 8.24 (1H, s, Ar)

EXAMPLE 4

Preparation of 2-(2-pyridylmethylthio)-5-trans-benzylideneimidazolin-4-one

Yield ratio: 64.5% Melting point: ~207° C (decomposition)

$^1$H-NMR ($CDCl_3$+DMSO-$d_6$, δ, ppm, TMS) 4.72, (2H, s, —$CH_2$—Ar), 6.80 (1H, s, =CH—Ar), 7.29~8.72 (9H, m, Ar)

EXAMPLE 5

Preparation of 2-(2-pyridylmethylthio)-5-trans-methylideneimidazolin-4-one

Yield ratio: 64.3% Melting point: 163°~165° C.

$^1$H-NMR ($CDCl_3$+DMSO-$d_6$, δ, ppm, TMS) 2.04 (3H, d, =CH—C$\underline{H}_3$), 4.61 (2H, s, —$CH_2$—Ar), 6.01~6.38 (1H, q, =C$\underline{H}$—$CH_3$), 7.19~8.68 (4H, s, Ar)

EXAMPLE 6

Preparation of 2-(4-methoxy-3,5-dimethyl-2-pyridylmethylthio)-5-trans-methylideneimidazolin-4-one Yield ratio: 52.0% Melting point: 204°~206° C.

$^1$H-NMR ($CDCl_3$+DMSO-$d_6$, δ, ppm, TMS) 2.08 (3H, d, =CH—C$\underline{H}_3$), 2.26 (3H, s, —Ar—$CH_3$), 2.36 (3H, s, Ar—$CH_3$), 3.79 (3H, s, —$OCH_3$), 4.58 (2H, s, —$CH_2$—Ar), 6.01~6.37 (1H, q, =C$\underline{H}$—$CH_3$), 8.17 (1H, s, Ar)

EXAMPLE 7

Preparation of 2-(2-pyridylmethylthio)-5,5-diphenylimidazolin-4-one

Yield ratio: 73.9% Melting point: 177°~179° C.

$^1$H-NMR (CDCl$_3$ δ, ppm, TMS) 4.59 (2H, s, —$CH_2$—Ar), 7.18~8.62 (14H, m, Ar)

EXAMPLE 8

Preparation of 2-(2-pyridylmethylthio)-5,5-dimethylimidazolin-4-one

Yield ratio: 67.4% Melting point 108°~109° C.

$^1$H-NMR ($CDCl_3$ δ, ppm, TMS) 1.38 (6H, s, —$CH_3$×2), 4.41 (2H, s, $CH_2$—Ar), 7.13~8.87 (4H, m, Ar)

EXAMPLE 9

Preparation of 2-(2-pyridylmethylthio)-5-methylimidazolin-4-one

Yield ratio: 51.4% Melting point: 96°~99° C.

$^1$H-NMR ($CDCl_3$+DMSO-$d_6$, δ, ppm, TMS) 1.43 (3H, d, —$CH_3$), 4.12 (1H, q, —CH—), 4.43 (2H, s, —$CH_2$—Ar), 7.13~8.72 (4H, m, Ar)

EXAMPLE 10

Preparation of 2-(2-pyridylmethylthio)-5-benzylimidazolin-4one

Yield ratio: 48.9% Melting point: 128°~130° C.

¹H-NMR (CDCl₃+DMSO-d₆, δ, ppm, TMS) 2.60~3.33 (2H, m, —CH₂—Ar), 3.93~4.43 (3H, m, CH₂—Ar+C—CH—N), 7.00~8.63 (9H, m, Ar)

EXAMPLE 11

Preparation of 2-(2-pyridylmethylthio)-5-methyl-5-phenylimidazolin-4-one

Yield ratio: 47.1% Melting point: 143°~144° C.

¹H-NMR (CDCl₃, δ, ppm, TMS) 1.66 (3H, S, —CH₃), 4.49 (2H, s, —CH₂—Ar), 7.25~8.66 (9H, m, Ar)

EXAMPLE 12

Preparation of 2-(2-pyridylmethylthio)-5,5-dipropylimidazolin-4-one

Yield ratio: 48.9% Melting point: 128°~130° C.

¹H-NMR (CDCl₃+DMSO-d₆, δ, ppm, TMS) 0.82 (3H, s, —CH₂—CH₃), 0.92 (3H, s, —CH₂—CH₃), 1.15~1.89 (8H, m, —CH₂×4), 4.37 (2H, s, —CH₂—Ar), 7.15~8.59 (4H, m, Ar)

EXAMPLE 13

Preparation of 2-(2-pyridylmethylthio)-5-ethyl-5-phenylimidazolin-4-one

Yield ratio: 45.7% Melting point: 126°~129° C.

¹H-NMR (CDCl₃, δ, ppm, TMS) 0.89 (3H, t, —CH₂—CH₃), 1.48 (2H, q, —CH₂—CH₃), 4.43 (2H, s, —CH₂—Ar), 7.16~8.63 (9H, m, Ar)

EXAMPLE 14

Preparation of 2-(2-pyridylmethylthio)-5-butyl-5-ethylimidazolin-4-one

Yield ratio: 56.3% Melting point: (syrup state)

¹H-NMR (CDCl₃, δ, ppm, TMS) 0.55~0.86 (6H, m, —CH₂—CH₃×2), 0.98~1.76 (8H, m, —CH₂—×4), 4.41 (2H, s, —CH₂—Ar), 7.11~8.63 (4H, m, Ar)

EXAMPLE 15

Preparation of 2-(2-pyridylmethylthio)-5-isobutyl-5-methylimidazolin-4-one

Yield ratio: 41.2% Melting point: 96°~99° C.

¹H-NMR (CDCl₃, δ, ppm, TMS) 0.82~1.36 (9H, m, —CH₃×3), 1.69~1.79 (3H, m, —CH₂—CH—), 4.39 (2H, s, —CH₂—Ar), 7.19~8.62 (4H, m, Ar)

EXAMPLE 16

Preparation of 2-(2-dimethylaminobenzylthio)-5,5-dimethylimidazolin-4-one

Initially, 1 g of 5,5-dimethyl-2-thiohydantoin was dissolved in 20 mL of dimethylsulfoxide, and 1.7 g of 2-dimethylaminobenzylchloride hydrochloride was added to the solution. The reaction mixture was stirred at the room temperature for one hour, and poured into 50 mL of water. The pH value of the solution was adjusted to 7–8 with diluted aqueous solution of 2N sodium hydroxide (NaOH). A precipitated sediment was extracted from the liquid, two times, using 50 mL of ethyl acetate (AcOEt). The AcOEt layer was successively washed with 50 mL of water and 50 mL of brine, dried over magnesium sulfate (MgSO₄), and concentrated in vacuo. The thus obtained residue was purified by column chromatography [developing solvent= CHCl₃:MeOH=20:1 (volume ratio, v/v)]. Recrystallized from diethyl ether gave the desired compound in the form of needle-like crystal. The yield of the compound was 1.2 g with a yield ratio of 62.4%, and its melting point was 113°~115° C.

A result of ¹H-NMR analysis of the compound is as follows:

¹H-NMR (CDCl₃, δ, ppm, TMS) 1.37 (6H, s, —CH₃×2), 2.70 {6H, s, —N(CH₃)₂}, 4.46 (2H, s, —CH₂—Ar), 6.93~7.60 (4H, m, Ar), 9.87 (1H, br. s, disappearance by addition of D₂O—NH)

In the following Examples 17–30, desired compounds were prepared using appropriate starting compounds, in the same manner as in Example 16. The yield ratio, melting point and ¹H-NMR analysis result of each of these compounds are indicated below.

EXAMPLE 17

Preparation of 2-(2-dimethylaminobenzylthio) imidazolin-4-one

Yield ratio: 48.1.% Melting point: 114°~116° C.

¹H-NMR (CDCl₃, δ, ppm, TMS) 2.78 {6H, s, —N(CH₃)₂}, 4.08 (2H, s, —CH₂—N), 4.31 (2H, s, —CH₂—Ar), 7.07~7.56 (4H, m, Ar)

EXAMPLE 18

Preparation of 2-(2-dimethylaminobenzylthio)-5-trans-benzylideneimidazolin-4-one Yield ratio: 68.6.% Melting point: 165°~167° C.

¹H-NMR (CDCl₃+DMSO-d₆, δ, ppm, TMS) 2.67 {6H, s, —N(CH₃)₂}, 4.67 (2H, s, C—CH₂—Ar), 6.77 (1H, s, =CH—Ar), 7.17~8.35 (9H, m, Ar)

EXAMPLE 19

Preparation of 2-(2-dimethylaminobenzylthio)-5-trans-methylideneimidazolin-4-one Yield ratio: 56.8.% Melting point: 97°~98° C.

¹H-NMR (CDCl₃, δ, ppm, TMS) 2.09 (3H, d, =CH—CH₃), 2.79 {6H, s, —N(CH₃)₂}, 4.47 (2H, s, —CH₂—Ar), 6.37 (1H, q, =CH—CH₃), 7.02~0.64 (4H, m, Ar)

EXAMPLE 20

Preparation of 2-(2-N-isobutyl-N-methylaminobenzylthio) imidazolin-4-one

Yield ratio: 36.9.% Melting point: (syrup state)

¹H-NMR (CDCl₃, δ, ppm, TMS) 0.96 (6H, d, —CH₃×2), 1.79~2.13 (1H, m, —CH—), 2.59~2.68 {5H, m, —N(CH₃)CH₂—}, 4.12 (2H, s, C—CH₂—N), 4.47 (2H, s, —CH₂—Ar), 7.01~7.63 (4H, m, Ar)

EXAMPLE 21

Preparation of 2-(2-N-isobutyl-N-methylaminobenzylthio)-5,5-dimethylimidazolin-4-one Yield ratio: 39.1.% Melting point: ~107° C.

¹H-NMR (CDCl₃, δ, ppm, TMS) 0.96 {6H, d, —CH(CH₃)₂}, 1.36 (6H, s, —CH₃×2), 1.72~2.13 {1H, m, —C$\underline{H}$(CH$_3$)$_2$}, 2.58~2.67 {5H, m, —N(CH$_3$)C$\underline{H}_2$—}, 4.49 (2H, s, —C$\underline{H}_2$—Ar), 6.86~7.66 (4H, m, Ar)

EXAMPLE 22

Preparation of 2-(2-dimethylaminobenzylthio)-5-methylimidazolin-4-one

Yield ratio: 44.0.% Melting point: 100°~102° C.

$^1$H-NMR (CDCl$_3$+DMSO-d$_6$, δ, ppm, TMS) 1.61 (3H, d, —CH$_3$), 2.69 {6H, s, —N(CH$_3$)$_2$}, 3.96 (1H, q, C—C$\underline{H}$—N), 4.49 (2H, s, —C$\underline{H}_2$—Ar), 6.86~7.66 (4H, m, Ar)

EXAMPLE 23

Preparation of 2-(2-dimethylaminobenzylthio)-5-benzylimidazolin-4-one

Yield ratio: 70.8.% Melting point: 124°~126.5° C.

$^1$H-NMR (CDCl$_3$, δ, ppm, TMS) 2.47 {6H, s, —N(CH$_3$)$_2$}, 2.68~3.37 (2H, m, —C$\underline{H}_2$—Ar), 3.93~4.30 (3H, m, —C$\underline{H}_2$—Ar+C—C$\underline{H}$—N), 6.90~7.43 (9H, m, Ar)

EXAMPLE 24

Preparation of 2-(2-dimethylaminobenzylthio)-5-methyl 5-phenylimidazolin-4-one

Yield ratio: 48.4.% Melting point: (amorphous)

$^1$H-NMR (CDCl$_3$, δ, ppm, TMS) 1.58 (3H, s, —CH$_3$), 2.63 {6H, s, —N(CH$_3$)$_2$}, 4.41 (2H, s, —C$\underline{H}_2$—Ar), 7.16~7.76 (9H, m, Ar)

EXAMPLE 25

Preparation of 2-(2-dimethylaminobenzylthio)-5-ethyl-5-methylimidazolin-4-one

Yield ratio: 57.9.% Melting point: 78°~81° C.

$^1$H-NMR (CDCl$_3$, δ, ppm, TMS) 0.71 (3H, t, —CH$_2$—C$\underline{H}_3$), 1.32 (3H, s, —CH$_3$), 1.74 (2H, q, —C$\underline{H}_2$—CH$_3$), 2.73 {6H, s, —N(CH$_3$)$_2$}, 4.36 (2H, s, —C$\underline{H}_2$—Ar), 6.88~7.53 (4H, m, Ar)

EXAMPLE 26

Preparation of 2-(2-dimethylaminobenzylthio)-5,5-dipropylimidazolin-4-one

Yield ratio: 36.6.% Melting point: 109°~110° C.

$^1$H-NMR (CDCl$_3$, δ, ppm, TMS) 0.80 (3H, s, —CH$_2$—C$\underline{H}_3$), 0.96 (3H, s, —CH$_2$—C$\underline{H}_3$), 1.29~1.92 (8H, m, —CH$_2$—×4), 2.74 {6H, s, —N(CH$_3$)$_2$}, 4.37 (2H, s, —C$\underline{H}_2$—Ar), 7.25~7.57 (4H, m, Ar)

EXAMPLE 27

Preparation of 2-(2-dimethylaminobenzylthio)-5-ethyl-5-phenylimidazolin-4-one

Yield ratio: 43.8.% Melting point: 104°~107° C.

$^1$H-NMR (CDCl$_3$, δ, ppm, TMS) 0.77 (3H, t, —CH$_2$—C$\underline{H}_3$), 1.93 (2H, q, —C$\underline{H}_2$—CH$_3$), 2.72 {6H, s, —N(CH$_3$)$_2$}, 4.40 (2H, s, —C$\underline{H}_2$—Ar), 6.93~7.47 (9H, m, Ar)

EXAMPLE 28

Preparation of 2-(2-dimethylaminobenzylthio)-5,5-diethylimidazolin-4-one

Yield ratio: 48.2.% Melting point: 98°~100° C.

$^1$H-NMR (CDCl$_3$, δ, ppm, TMS) 0.70 (6H, t, —CH$_2$—C$\underline{H}_3$×2), 1.75 (4H, q, —C$\underline{H}_2$—CH$_3$×2), 2.71 {6H, s, —N(CH$_3$)$_2$}, 4.38 (2H, s, —C$\underline{H}_2$—Ar), 6.91~7.5 (4H, m, Ar)

EXAMPLE 29

Preparation of 2-(2-dimethylaminobenzylthio)-5-butyl-5-ethylimidazolin-4-one

Yield ratio: 43.8.% Melting point: (syrup state)

$^1$H-NMR (CDCl$_3$, δ, ppm, TMS) 0.71 (6H, m, —CH$_2$—C$\underline{H}_3$×2), 1.04~1.78 (8H, m, —CH$_2$—×4), 2.73 {6H, s, —N(CH$_3$)$_2$}, 4.37 (2H, s, —C$\underline{H}_2$—Ar), 7.13~7.66 (4H, m, Ar)

EXAMPLE 30

Preparation of 2-(2-dimethylaminobenzylthio)-5-isobutyl5-methylimidazolin-4-one

Yield ratio: 72.0.% Melting point: (syrup state)

$^1$H-NMR (CDCl$_3$, δ, ppm, TMS) 0.85~1.32 (9H, m, —CH$_3$×3), 1.67~1.81 (3H, m, —C$\underline{H}_2$—C$\underline{H}$—), 2.72 {6H, s, —N(CH$_3$)$_2$}, 4.42 (2H, s, —C$\underline{H}_2$—Ar), 7.19~7.62 (4H, m, Ar)

EXAMPLE 31

Preparation of maleic acid salt of 2-(2-dimethylaminobenzylthio)-5,5-dimethylaminobenzylthio-5,5-dimethylimidazolin-4-one Initially, 1.5 g of 2-(2-dimethylaminobenzylthio)-5,5-dimethylimidazolin-4-one which was obtained in Example 16 was dissolved in 50 mL of acetone, and 0.63 g of maleic acid was added to the solution. The solution was stirred for 20 minutes at the room temperature, and concentrated in vacuo. The thus obtained residue was crystallized from EtOH-petroleum-ether to give the desired compound, namely, mono maleate of 2-(2-dimethylaminobenzylthio)-5,5-dimethylimidazolin-4-one, in the form of needle-like crystal. The yield of this compound was 1.6 g with a yield ratio of 75.2%, and its melting point was not higher than 105° C.

A result of an elemental analysis of the compound is as follows:

Elemental analysis: C$_{14}$H$_{19}$N$_3$OS.C$_4$H$_4$O$_4$.1/4H$_2$O

Calculated values: C:54.33%, H:5.95%, N:10.56%

Measured values: C:54.46%, H:5.76%, N:10.55%

EXAMPLE 32

Preparation of 2-(2-dimethylaminobenzylthio)-5,5-dimethylimidazolin-4-one hydrochloride Hydrogen chloride gas was introduced to a cold solution of 0.27 g of 2-(2-dimethylaminobenzylthio)-6,5-dimethylimidazolin-4-one in 30 mL of diethyl ether while the solution was stirred. The precipitate was filtered, and washed with diethyl ether to give the desired compound in the form of a powder. The yield of this compound was 0.25 g with a yield ratio of 81.8%, and the melting point was 113°~114° C.

A result of an elemental analysis of the compound is as follows:

Element analysis: C$_{14}$H$_{19}$N$_3$OS.2HCl. H$_2$O

Calculated values: C:45.65%, H:6.29%, N:11.41%
Measured values: C:45.62%, H:6.19%, N:11.59%

EXAMPLE 33

1-N-acetyl-2-(2-dimethylaminobenzylthio)-5,5-dimethyl-2-imidazolin-4-one

Initially, 4.18g of 2-dimethylaminobenzylchloride hydrochloride was added to a solution of 3.43 g of 1-N-acetyl-5,5-dimethyl-2-thiohydantoin in 50 mL of N,N-dimethylsulfoxide. The reaction mixture was stirred for one hour at the room temperature and poured into 100 mL of water. The pH of the solution was adjusted to 7–8 with a diluted aqueous solution of NaOH and extracted. The precipitate was extracted with 100 mL of ethyl acetate (AcOEt). The thus obtained AcOET layer was successively washed two times with 100 mL of water and 100 mL of brine, dried over magnesium sulfate ($MgSO_4$), and concentrated in vacuo. The thus obtained residue was purified by column chromatography (using $CHCL_3$ as a developing solvent). Recrystallized from diethyl ether-n-hexane gave the desired compound in the form of needle-like crystal. The yield of this compound was 3.4 g with a yield ratio of 57.6%, and the melting point was 99°–100° C.

A result of a $^1$H-NMR analysis of the compound is as follows:
$^1$H-NMR ($CDCl_3$, δ, ppm, TMS) 2.41 (6H, s, —$CH_3$×2), 2.50 (3H, s, —$COCH_3$), 2.68 {6H, s, —$N(CH_3)_2$}, 4.43 (2H, s, —$CH_2$—Ar), 6.87–7.67 (4H, m, Ar)

EXAMPLE 34

1-N-acetyl-2-(2-dimethylaminobenzylthio)-5-ethyl-5-methyl-2-imidazolin-4-one

In the present Example, 2.27 g of 2-dimethylaminobenzylchloride hydrochloride and 2.0 g of 1-N-acetyl-5-ethyl-5-methyl-2-thiohydantoin were reacted following the procedure of Example 33. The desired compound was obtained in the form of needle-like crystal. The yield of this compound was 1.37 g with a yield ratio of 41.1%, and the melting point was 83°–85° C.

A result of a $^1$H-NMR analysis of this compound is as follows:
$^1$H-NMR ($CDCl_3$, δ, ppm, TMS) 0.71 (3H, t, —$CH_2$—$CH_3$), 1.58 (3H, s, —$CH_3$), 2.07 (2H, q, —$CH_2$—$CH_3$), 2.33 (3H, s, —$COCH_3$), 2.67 {6H, s, —$N(CH_3)_2$}, 4.46 (2H, s, —$CH_2$—Ar), 6.88–7.68 (4H, m, Ar)

EXAMPLE 35

1-N-methyl-2-(2-dimethylaminobenzylthio)-4,4-dimethyl-2-imidazolin-5-one

To a solution of 0.5 g of 2-(2-dimethylaminobenzylthio)-5,5-dimethylimidazolin-4-one in 20 mL of N,N-dimethylformamide, there was added 60% sodium hydride in 0.09 g of mineral oil at −10° C. After the mixture was stirred for 15 minutes, 1 mL of methyl iodide was added to the mixture, and the stirring was continued for one hour. To the reaction mixture, there were added 100 mL of ethyl acetate (AcOEt) and 100 mL of water. The AcOEt layer was separated. The separated AcOEt layer was washed three times with 50 mL of brine, dried over magnesium sulfate ($MgSO_4$), and concentrated in vacuo. The residue was purified by column chromatography (using $CHCl_3$ as a developing solvent), to give the desired compound in the form of a syrup. The yield of this compound was 0.41 g with a yield ratio of 78.1%.

A result of $^1$H-NMR analysis of the compound is as follows:
$^1$H-NMR ($CDCl_3$, δ, ppm, TMS) 1.40 (6H, s, —$CH_3$×2), 2.77 {6H, s, —$N(CH_3)_2$}, 3.03 (3H, s, —$NCH_3$), 4.57 (2H, s, —$CH_2$—Ar), 6.87–7.70 (4H, m, Ar)

EXAMPLE 36

4-(2-dimethylaminobenzylthio)-5,5-dimethyl-3-imidazolin-2-one

Initially, 2.5 g of 2-dimethylaminobenzylchloride hydrochloride was added to a solution of 1.5 g of 5,5-dimethyl-4-thiohydantoin in 50 mL of methanol (MeQH). The reaction mixture was stirred for two hours at the room temperature and concentrated in vacuo. To the residue, there was added 100 mL of $CHCl_3$. The residue was washed two times with 100 mL of aqueous solution of $NaHCO_3$, dried over $MgSO_4$ and concentrated in vacuo. The residue purified by column chromatography [$CHCl_3$:MeOH=100:1 (v/v)]. Recrystallized from diethyl ether gave the desired compound in the form of needle-like crystal. The yield of this compound was 2 g with a yield ratio of 69.1%, and the melting point was 160°–162° C.

A result of a $^1$H-NMR analysis of the compound is as follows:
$^1$H-NMR ($CDCl_3$, δ, ppm, TMS) 1.48 (6H, s, —$CH_3$×2), 2.72 {6H, s, —$N(CH_3)_2$}, 4.67 (2H, s, —$CH_2$—Ar), 6.96–7.64 (4H, m, Ar)

EXAMPLE 37

1-N-methyl-4-(2-dimethylaminobenzylthio)-5,5-dimethyl-3-imidazolin-2-one

Initially, 0.5 g of 4-(2-dimethylaminobenzylthio)-5,5-dimethyl-3-imidazolin-2-one was reacted with 1 mL of methyl iodide following the procedure used in Example 35. The desired compound was obtained in the form of a syrup. The yield of this compound was 0.43 g with a yield ratio of 81.9%. A result of a $^1$H-NMR analysis of the compound is as follows:
$^1$H-NMR ($CDCl_3$, δ, ppm, TMS) 1.33 (6H, s, —$CH_3$×2), 2.67 {6H, s, —$N(CH_3)_2$}, 2.88 (3H, s, —$NCH_3$), 4.62 (2H, s, —$CH_2$—Ar), 6.90–7.48 (4H, m, Ar)

EXAMPLE 38

4-(2-dimethylaminobenzylthio)-5-ethyl-5-methyl-3-imidazolin-2-one

In the present Example, 2.3 g of 2-dimethylaminobenzylchloride hydrochloride and 1.5 g of 5-ethyl-5-methyl-4-thiohydantoin were reacted following the procedure used in Example 36. Crystallization from diethyl ether-n-hexane gave the desired compound in the form of a needle-like crystal. The yield of this compound was 1.9 g with a yield ratio of 68.6%, and the melting point was 111°–113° C.

A result of a $^1$H-NMR analysis of the compound is as follows:
$^1$H-NMR ($CDCl_3$, δ, ppm, TMS) 0.74 (3H, t, —$CH_2$—$CH_3$), 1.45 (3H, s, —$CH_3$), 1.83 (2H, q, —$CH_2$—$CH_3$), 2.71{6H, s, —$N(CH_3)_2$}, 4.69 (2H, s, —$CH_2$—Ar), 6.91–7.68 (4H, m, Ar)

EXAMPLE 39

2-(2-dimethylaminobenzylthio)-5,5-dimethylimidazolin-4-thione and 2,4-bis(2-dimethylaminobenzylthio)-5,5-dimethyl-5H-imidazole (a) Initially, a solution of 9.1 g of 2-dimethylaminobenzylchloride hydrochloride in 50 mL of EtOH was added to a solution of 7 g of 5,5-dimethyl-2,4-dithiohydantoin in 100 mL of ethanol (EtOH). The reaction mixture was stirred for 1.5 hour at the room temperature and concentrated in vacuo. To the residue, there was added 100 mL of chloroform ($CHCl_3$). The residue was then washed with an aqueous solution of potassium carbonate ($CaCO_3$), dried over magnesium sulfate ($MgSO_4$), and concentrated in vacuo. The residue was chromatographed on a column of silica gel ($CHCl_3$). From the earlier fractions, 2,4-bis(2-dimethylaminobenzylthio)-5,5-dimethyl-5H-imidazole was isolated as a syrup. The yield of this compound was 1.1 g with a yield ratio of 5.9%.

A result of a $^1$H-NMR analysis of the compound is as follows:

$^1$H-NMR ($CDCl_3$, δ, ppm, TMS) 1.40 (6H, s, —$CH_3$×2), 2.70 {6H, s, —$N(CH_3)_2$}, 2.73 {6H, s, —$N(CH_3)_2$}, 4.57 (2H, s, —$CH_2$—Ar), 4.63 (2H, s, —$CH_2$—Ar), 6.80~7.73 (8H, m, Ar)

From the later fractions, 2-(2-dimethylaminobenzylthio)-5,5-dimethylimidazolin-4-thione was isolated. Crystallized from diethyl ether-petroleum ether gave the desired compound in the form of a needle-like crystal. The yield of this compound was 6.1 g with a yield ratio of 47.6%, and the melting point was 139°–140° C.

A result of a $^1$H-NMR analysis of the compound is as follows:

$^1$H-NMR ($CDCl_3$, δ, ppm, TMS) 1.43 (6H, s, —$CH_3$×2), 2.87 {6H, s, —$N(CH_3)_2$}, 4.37 (2H, s, —$CH_2$—Ar), 7.20~7.57 (4H, m, Ar)

(b) Initially, 11 g of 2-dimethylaminobenzylchloride hydrochloride was added to a solution of 8 g of 5,5-dimethyl-2,4-dithiohydantoin in 200 mL of chloroform ($CHCl_3$) at about 60° C. The reaction mixture was stirred for 30 minutes and washed with an aqueous solution of $NaHCO_3$, dried over $MgSO_4$, and concentrated in vacuo. The residue was treated following the procedure used for the compound (a). As a result, the desired compound of 2-(2-dimethylaminobenzylthio)-5,5-dimethylimidazolin-4-thione was isolated by column chromatography. The yield of this compound was 9.1 g with a yield ratio of 62.1%. Further, the desired compound of 2,4-bis(2-dimethylaminobenzylthio)-5,5-dimethyl-5H-imidazole was isolated. The yield of this compound was 1.2 g with a yield ratio of 5.6%.

In the following Examples 40–54, desired compounds were prepared from appropriate starting compounds, in the same manner as in Example 39. The yield ratio, melting point and $^1$H-NMR analysis result of each of these compounds are indicated below. It is noted that 2,4-bis substituents are quantitatively obtained with the equivalent amount of a halide being at least 2 with respect to dithiohydantoin. These examples will be described later.

EXAMPLE 40

2-(2-dimethylaminobenzylthio)-5,5-diethylimidazolin-4-thione

Yield ratio: 62.5% Melting point: 135°–136° C. $^1$H-NMR ($CDCl_3$, δ, ppm, TMS) 0.58 (6H, t, —$CH_2$—$CH_3$×2), 1.66~2.05 (4H, m, —$CH_2$—$CH_3$×2), 2.81 {6H, s, —$N(CH_3)_2$}, 4.31 (2H, s, —$CH_2$—Ar), 7.00~7.49 (4H, m, Ar)

EXAMPLE 41

2-(2-dimethylaminobenzylthio)-5-phenyl-5-methylimidazolin-4-thione

Yield ratio: 56.9% Melting point: (amorphous) $^1$H-NMR ($CDCl_3$, δ, ppm, TMS) 1.82 (3H, s, —$CH_3$), 2.79 {6H, s, —$N(CH_3)_2$}, 4.30(2H, s, —$CH_2$—Ar), 7.17~7.49 (9H, m, Ar)

EXAMPLE 42

2-(2-dimethylaminobenzylthio)-5-ethyl-5-methylimidazolin-4-thione

Yield ratio: 52.9% Melting point: 139°~141° C.

$^1$H-NMR ($CDCl_3$, δ, ppm, TMS) 0.72 (3H, t, —$CH_2$—$CH_3$), 1.39 (3H, s, —$CH_3$), 1.86(2H, q, $CH_2$—$CH_3$), 2.82 {6H, s, —$N(CH_3)_2$}, 4.32 (2H, s, —$CH_2$—Ar), 7.17~7.44 (4H, m, Ar)

EXAMPLE 43

2-(2-N-isobutyl-N-methylaminobenzylthio)-5,5-dimethylimidazolin-4-thione

Yield ratio: 38.2% Melting point: 128°~130° C.

$^1$H-NMR ($CDCl_3$, δ, ppm, TMS) 0.97 {6H, d, —CH($CH_3)_2$}, 1.43 (6H, s, —$CH_3$×2), 1.61~2.02 {1H, m, —$CH(CH_3)_2$}, 2.62~2.74 {5H, m, —$N(CH_3)CH_2$—}, 4.50 (2H, s, —$CH_2$—Ar), 7.06~7.56 (4H, m, Ar)

EXAMPLE 44

2-(8-quinolynylmethylthio)-5,5-dimethylimidazolin-4-thione

Yield ratio: 51.3% Melting point: 84°~86° C. $^1$H-NMR ($CDCl_3$, δ, ppm, TMS) 1.34 (6H, s, —$CH_3$×2), 5.04 (2H, s, —$CH_2$—Ar), 7.39~9.10 (6H, m, Ar)

EXAMPLE 45

2-(3-dimethylaminobenzylthio)-5,5-dimethylimidazoline-4-thione

Yield ratio: 1.0% Melting point: 168°~170° C.

$^1$H-NMR ($CDCl_3$, δ, ppm, TMS) 1.43 (6H, s, —$CH_3$×2), 2.91 {6H, s, —$N(CH_3)_2$}, 4.34 (2H, s, —$CH_2$—Ar), 6.54~7.29 (4H, m, Ar)

EXAMPLE 46

2-(2-N-ethyl-N-methylaminobenzylthio)-5,5-dimethylimidazolin-4-thione

Yield ratio: 31.9% Melting point: 145°~146° C.

$^1$H-NMR ($CDCl_3$, δ, ppm, TMS) 1.17 (3H, t, —$CH_2$—$CH_3$), 1.42 (6H, s, —$CH_3$×2), 2.84~3.07 (5H, m, —$N(CH_3)CH_2$—{, 4.31 (2H, s, —$CH_2$—Ar), 6.56~7.31 (4H, m, Ar)

EXAMPLE 47

2-(2-dimethylamino-5-methylbenzylthio)-5,5-dimethylimidazolin-4-thione

Yield ratio: 21.8% Melting point: 130°~131° C.

$^1$H-NMR ($CDCl_3$, δ, ppm, TMS) 1.42 (6H, s, —$CH_3$×2), 2.31 (3H, s, —Ar—$CH_3$), 2.82 (6H, s, —$N(CH_3)_2$}, 4.25 (2H, s, —$CH_2$—Ar), 7.12~7.25 (3H, m, Ar)

EXAMPLE 48

2-(2-dimethylamino-3-methylbenzylthio)-5,5-dimethylimidazolin-4-thione

Yield ratio: 14.3% Melting point: 113°~115° C.

$^1$H-NMR (CDCl$_3$, δ, ppm, TMS) 1.46 (6H, s, —CH$_3$×2), 2.33 (3H, s, Ar—CH$_3$), 2.84 {6H, s, —N(CH$_3$)$_2$}, 4.41 (2H, s, —CH$_2$—Ar), 6.91~7.34 (3H, m, Ar)

EXAMPLE 49

2-(2-dimethylamino-6-methylbenzylthio)-5,5-dimethylimidazolin-4-thione

Yield ratio: 19.9% Melting point: 143°~145° C.

$^1$H-NMR (CDCl$_3$s, δ, ppm, TMS) 1.43 (6H, s, —CH$_3$×2), 2.39 (3H, s, Ar—CH$_3$), 2.84 {6H, s, —N(CH$_3$)$_2$}, 4.35 (2H, s, —CH$_2$—Ar), 6.93~7.33 (3H, m, Ar)

EXAMPLE 50

2-(5-chloro-2-dimethylaminobenzylthio)-5,5-dimethylimidazolin-4-thione

Yield ratio: 27.1% Melting point: 145°~147° C.

$^1$H-NMR (CDCl$_3$, δ, ppm, TMS) 1.44 (6H, s, —CH$_3$×2), 2.77 {6H, s, —N(CH$_3$)$_2$}, 4.33 (2H, s, —CH$_2$—Ar), 7.19~7.50 (3H, m, Ar)

EXAMPLE 51

2-(4-chloro-2-dimethylaminobenzylthio)-5,5-dimethylimidazolin-4-thione

Yield ratio: 26.2% Melting point: 157°~159° C.

$^1$H-NMR (CDCl$_3$, δ, ppm, TMS) 1.43 (6H, s, —CH$_3$×2), 2.83 {6H, s, —N(CH$_3$)$_2$ }, 4.33 (2H, s, —CH$_2$—Ar), 7.19~78.37 (3H, m, Ar)

EXAMPLE 52

2-(2-dimethylamino-5-methoxybenzylthio)-5,5-dimethylimidazolin-4-thione

Yield ratio: 14.6% Melting point: 102°~103° C.

$^1$H-NMR (CDCl$_3$, δ, ppm, TMS) 1.42 (6H, s, —CH$_3$×2), 2.80 {6H, s, —N(CH$_3$)$_2$}, 3.81 (3H, s, —OCH$_3$), 4.27 (2H, s, —CH$_2$—Ar), 6.77~7.45 (3H, m, Ar)

EXAMPLE 53

2-(2-dimethylamino-4-fluorobenzylthio)-5,5-dimethylimidazolin-4-thione

Yield ratio: 18.9% Melting point: 133°~135° C. $^1$H-NMR (CDCl$_3$, δ, ppm, TMS) 1.41 (6H, s, —CH$_3$×2), 2.80 {6H, s, —N(CH$_3$)$_2$}, 4.31 (2H, s, —CH$_2$—Ar), 6.89~7.51 (3H, m, Ar)

EXAMPLE 54

2-(2-N-methyl-N-trifluoroacetylaminobenzylthio)-5,5-dimethylimidazolin-4-thione

Yield ratio: 18.9% Melting point: 191°~192° C.

$^1$H-NMR (CDCl$_3$+DMSO-d$_6$, δ, ppm, TMS) 1.40 (6H, s, —CH$_3$×2), 3.40 (3H, s, —NCH$_3$), 4.43 (2H, s, —CH$_2$—Ar), 7.20~7.83 (4H, m, Ar)

EXAMPLE 55

2-(2-pyridylmethylthio)-5,5-dimethylimidazolin-4-thione and 2,4-bis(2-pyridylmethylthio)-5,5-dimethyl-5H-imidazole Initially, 2.7 g of 2-chloromethylpyridine hydrochloride was added to a solution of 2.4g of 5,5-dimethyl-2,4-dithiohydantoin in 17 mL of 2N aqueous solution of NaOH. The reaction mixture was stirred for one hour at the room temperature, and extracted with 100 mL of chloroform (CHCl$_3$). The CHCl$_3$ layer was dried over MgSO$_4$ and concentrated in vacuo. The residue was purified by column chromatography (using CHCl$_3$ as a developing solvent). As a result, 2-(2-pyridylmethylthio) was initially obtained. From the earlier fractions, the desired compound of 2-(2-pyridylmethylthio)-5,5-dimethylimidazolin-4-thione was isolated in the form of a syrup. The yield of this compound was 1.02 g with a yield ratio of 27.1%.

A result of a $^1$H-NMR analysis of the compound is as follows:

$^1$H-NMR (CDCl$_3$, δ, ppm, TMS) 1.47 (6H, s, —CH$_3$×2), 4.48 (2H, s, —CH$_2$—Ar), 7.15~8.68 (4H, m, Ar)

From the latter fractions, the desired component of 2,4-bis(2-pyridylmethylthio)-5,5-dimethyl-5H-imidazole was isolated in the form of a syrup. The yield of this compound was 0.22 g with a yield ratio of 4.29%.

A result of a $^1$H-NMR analysis of the compound is as follows: $^1$H-NMR (CDCl$_3$, δ, ppm, TMS) 1.34 (6H, s, —CH$_3$×2), 4.54 (2H, s, —CH$_2$—Ar), 4.57 (2H, s, —CH$_2$—Ar), 7.07~8.66 (8H, m, Ar)

EXAMPLE 56

4-(2-N-acetylaminobenzylthio)-5,5-dimethylimidazolin-2-thione and 2,4-bis(2-N-acetylaminobenzylthio)-5,5-dimethyl-5H-imidazole initially, 1.5 g of 2-N-acetylaminobenzylchloride was added to a mixture of 1.5 g of 5,5-dimethyl-2,4-dithiohydantoin and 1.3 g of sodium methoxide in 30 mL of methanol (MeOH). The reaction mixture was stirred at the room temperature for three hours, and concentrated in vacuo. To the residue, there was added 50 mL of CHCl$_3$, and the mixture was washed two times each with 50 mL of water. The CHCl$_3$ layer was dried over MgSO$_4$ and concentrated in vacuo. The residue was chromatographed on a column of silica gel (CHCL$_3$. From the earlier fractions, the desired component of 2,4-bis(2-N-acetylaminobenzylthio)-5,5-dimethyl-5H-imidazole was isolated, which was crystallized from CHCl3-diethyl ether in the form of a needle-like crystal. The yield of this compound was 1.14 g with a yield ratio of 46.0%, and the melting point was 87°–88° C.

A result of a $^1$H-NMR analysis of the compound is as follows:

$^1$H-NMR (CDCl$_3$, δ, ppm, TMS) 1.35 (6H, s, —CH$_3$×2), 2.23 (3H, s, —COCH$_3$), 2.30 (3H, s, —COCH$_3$), 4.27 (2H, s, —CH$_2$—Ar), 4.30 (2H, s, —CH$_2$—Ar), 7.17~7.93 (8H, m, Ar)

From the latter fractions, the desired component of 4-(2-N-acetylaminobenzylthio)-5,5-dimethylimidazolin-2-thione was isolated, which was crystallized from CH$_2$Cl$_2$-n-hexane in the form of a needle-like crystal. The yield of this compound was 0.43 g with a yield ratio of 12.4%, and the melting point was 186°–188° C.

A result of a $^1$H-NMR analysis of this compound is as follows:

$^1$H-NMR (CDCl$_3$+DMSO-d$_6$, δ, ppm, TMS) 1.43 (6H, s, —CH$_3$×2), 2.40 (3H, s, —COCH$_3$), 4.13 (2H, s, —CH$_2$—Ar), 7.17~7.77 (4H, m, Ar)

EXAMPLE 57

2-(2-N-benzoylaminobenzylthio)-5,5-dimethylimidazolin-4-thione, 4-(2-N-benzoylaminobenzylthio)-5,5-dimethyl 3-imidazolin-2-thione, and 2,4-bis(2-N-benzoylaminobenzylthio)-5,5-dimethyl-5H-imidazole Initially, 1.7 g of 2-N-benzoylaminobenzylchloride was added to a mixture of 1 g of 5,5-dimethyl-2,4-dithiohydantoin and 0.4 g of sodium methoxide in 30 mL of MeOH. The reaction mixture was stirred at the room temperature for eight hours, and concentrated in vacuo. The residue was treated following the procedure used in Example 56, and chromatographed on a column of silica gel ($CH_2Cl_2$). Initially, 2,4-bis(2-N-benzoylaminobenzylthio)-5,5-dimethyl-5H-imidazole was eluted, and crystallized from $CH_2Cl_2$-n-hexane, in the form of a needle-like crystal. The yield of this compound was 0.58 g with a yield ratio of 16.1%, and the melting point was 182°–183° C.

A result of a $^1$H-MNR analysis of the compound is as follows:

$^1$H-NMR ($CDCl_3$, δ, ppm, TMS) 1.07 (6H, s, —$CH_3$×2), 4.23 (2H, s, —$CH_2$—Ar), 4.33 (2H, s, —$CH_2$—Ar), 7.20~8.17 (18H, m, Ar)

Then, 2-(2-N-benzoylaminobenzylthio)-5,5-dimethylimidazolin-4-thione was eluted, and crystallized from $CH_2Cl_2$-diethyl ether, in the form of a needle-like crystal. The yield of this compound was 0.18 g with a yield ratio of 7.8%, and the melting point was 174°–175° C.

A result of a $^1$H-NMR analysis of the compound is as follows:

$^1$H-NMR ($CDCl_3$, δ, ppm, TMS) 1.20 (6H, s, —$CH_3$×2), 4.30 (2H, s, —$CH_2$—Ar), 7.03~8.20 (9H, m, Ar)

Finally, 4-(2-N-benzoylaminobenzylthio)-5,5-dimethyl-3-imidazolin-2-thione was eluted, and crystallized from $CH_2Cl_2$, in the form of a needle-like crystal. The yield of this compound was 0.22 g with a yield ratio of 9.6%, and the melting point was 199°–200° C. A result of a $^1$H-NMR analysis of the compound is as follows:

$^1$H-NMR ($CDCl_3$+DMSO-$d_6$, δ, ppm, TMS) 1.33 (6H, s, —$CH_3$×2), 4.53 (2H, s, —$CH_2$—Ar), 7.20~8.43 (9H, m, Ar)

EXAMPLE 58

2-(2-N-trifluoroacetylaminobenzylthio)-5,5-dimethylimidazolin-4-thione, and 2,4-bis(2-N-trifluoroacetylaminobenzylthio)-5,5-dimethyl-5H-imidazole Initially, 3 g of 2-N-trifluoroacetylaminobenzylchloride was added to a mixture of 2 g of 5,5-dimethyl-2,4-dithiohydantoin and 0.8 g of MeOH. The reaction mixture was stirred at the room temperature for eight hours, and concentrated in vacuo. The residue was treated following the procedure used in Example 56, and chromatographed on a column of silica gel ($CH_2Cl_2$). From the earlier fractions, 2,4-bis(2-N-trifluoroacetylaminobenzylthio)-5,5-dimethyl-5H-imidazole was isolated, which was crystallized from $CH_2Cl_2$-n-hexane, in the form of a needle-like crystal. The yield of this compound was 0.89 g with a yield ratio of 13%, and the melting point was 73°–74° C.

A result of a $^1$H-NMR analysis of the compound is as follows:

$^1$H-NMR ($CDCl_3$, δ, ppm, TMS) 1.27 (6H, s, —$CH_3$×2), 4.13 (2H, s, —$CH_2$—Ar), 4.17 (2H, s, —$CH_2$—Ar), 6.97~7.70 (8H, m, Ar)

From the latter fractions, 2-(2-N-trifluoroacetylaminobenzylthio)-5,5-dimethylimidazolin-4-thione was isolated, which was crystallized from $CH_2Cl_2$-petroleum ether, in the form of a needle-like crystal. The yield of this compound was 0.96 g with a yield ratio of 21.0%, and the melting point was 174°–175° C.

A result of a $^1$H-NMR analysis of this compound is as follows:

$^1$H-NMR ($CDCl_3$+DMSO-$d_6$, δ, ppm, TMS) 1.35 (6H, s, —$CH_3$×2), 4.20 (2H, s, —$CH_2$—Ar), 7.10~7.80 (9H, m, Ar)

EXAMPLE 59

2-(2-aminobenzylthio)-5,5-dimethylimidazolin-4-thione

Initially, 1.2 g of $K_2CO_3$ and 10 mL of water were added to a solution of 1.0 g of 2-(2-N-trifluoroacetylaminobenzylthio)-5,5-dimethylimidazolin-4-thione in 30 mL of MeOH. The reaction mixture was stirred at the room temperature for two days, and extracted with 100 mL of $CHCl_3$. The $CHCl_3$ layer was dried over $MgSO_4$ and concentrated in vacuo. The residue was crystallized from $CH_2Cl_2$-petroleum ether to give the desired compound in the form of a needle-like crystal. The yield of this compound was 0.39 g with a yield ratio of 53%, and the melting point was 103°–104° C.

A result of a $^1$H-NMR analysis of the compound is as follows:

$^1$H-NMR ($CDCl_3$+DMSO-$d_6$, δ, ppm, TMS) 1.40 (6H, s, —$CH_3$×2), 4.37 (2H, s, —$CH_2$—Ar), 6.53~7.48 (4H, m, Ar)

EXAMPLE 60

4-(2-quinolinylmethylthio)-5,5-dimethylimidazolin-2-thione, and 2,4-bis(2-quinolinylmethylthio)-5,5-dimethyl-5H-imidazole initially, 2.7 g of 2-chloromethylquinoline hydrochloride was added to a mixture of 2 g of 5,5-dimethyl-2,4-dithiohydantoin and 3.6 g of sodium methoxide in 100 mL of MeOH. The reaction mixture was stirred at the room temperature for five hours, and concentrated in vacuo. The residue was treated following the procedure used in Example 56, and chromatographed on a column of silica gel ($CHCl_3$). From the earlier fractions, 2,4-bis(2-quinolynylmethylthio)-5,5-dimethyl-5H-imidazole was isolated, which was crystallized from diethyl ether-petroleum ether, in the form of a needle-like crystal. The yield of this compound was 2.1 g with a yield ratio of 38%, and the melting point was 105°–107° C.

A result of a $^1$H-NMR analysis of the compound is as follows:

$^1$H-NMR ($CDCl_3$, δ, ppm, TMS) 1.37 (6H, s, —$CH_3$2), 4.73 (4H, s, —$CH_2$—Ar×2), 7.23~8.17 (12H, m, Ar)

From the latter fractions, 4-(2-quinolinylmethylthio)-5,5-dimethylimidazolin-2-thione was isolated, which was crystallized from diethyl ether-petroleum ether, in the form of a needle-like crystal. The yield of this compound was 1.8 g with a yield ratio of 47.9%, and the melting point was 188°–189° C. A result of a $^1$H-NMR analysis of the compound is as follows:

$^1$H-NMR ($CDCl_3$, δ, ppm, TMS) 1.45 (6H, s, —$CH_3$×2), 4.89 (2H, s, —$CH_2$—Ar), 7.46~8.42 (6H, m, Ar)

EXAMPLE 61

4-(3-dimethylaminobenzylthio)-5,5-dimethylimidazolin-2-thione, and 2,4-bis(3-dimethylaminobenzylthio)-5,5-dimethyl-5H-imidazole Initially, 2.94 g of 3-dimethylaminobenzylchloride hydrochloride was added to a mixture of 1.6 g of 5,5-dimethyl-2,4-dithiohydantoin and 1.3 g of sodium methoxide in 50 mL of methanol (MeOH). The reaction mixture was stirred at the room temperature for one hour, and concentrated in vacuo. The residue was treated following the procedure used in Example 56, and chromatographed on a column of silica gel ($CHCl_3$). From the earlier fractions, 2,4-bis(3-dimethylaminobenzylthio)-5,5-dimethyl-5H-imidazole was isolated, in the form of a syrup. The yield of this compound was 0.31 g with a yield ratio of 7.4%.

A result of a $^1$H-NMR analysis of the compound is as follows:

$^1$H-NMR ($CDCl_3$, δ, ppm, TMS) 1.35 (6H, s, —$CH_3$×2), 2.91 {12H, s, —N($CH_3$)$_2$×2}, 4.28 (2H, s, —$CH_2$—Ar), 4.30 (2H, s, —$CH_2$—Ar), 6.53~7.31 (8H, m, Ar)

From the latter fractions, 4-(3-dimethylaminobenzylthio)-5,5-dimethylimidazolin-2-thione was isolated, which was crystallized from diethyl ether-n-hexane, in the form of a needle-like crystal. The yield of this compound was 0.6 g with a yield ratio of 20.5%, and the melting point was 178°–179° C.

A result of a $^1$H-NMR analysis of the compound is as follows:

$^1$H-NMR ($CDCl_3$, δ, ppm, TMS) 1.48 (6H, s, —$CH_3$×2), 2.95 {6H, s, —N($CH_3$)$_2$}, 4.52 (2H, s, —$CH_2$—Ar), 6.56~7.31 (4H, m, Ar)

EXAMPLE 62

2,4-bis-(8-quinolinylmethylthio)-5,5-dimethyl-5H-imidazole

Initially, 3 g of 8-bromomethylquinoline was added to a solution of 1 g of 5,5-dimethyl-2,4-dithiohydantoin in 50 mL of ethanol (EtOH). The reaction mixture was stirred at the room temperature for 1.5 hour, and concentrated in vacuo. To the residue, 100 mL of $CHCl_3$ was added. The mixture was washed with an aqueous solution of $K_2CO_3$, dried over $MgSO_4$ and concentrated in vacuo. The residue was purified by column chromatograph ($CHCl_3$). Recrystallization from diethyl ether gave the desired compound in the form of a needle-like crystal. The yield of this compound was 2.3 g with a yield ratio of 83.3%, and the melting point was 101°–104° C.

A result of a $^1$H-NMR analysis of the compound is as follows:

$^1$H-NMR ($CDCl_3$, δ, ppm, TMS) 1.33 (6H, s, —$CH_3$×2), 5.08 (2H, s, —$CH_2$—Ar), 5.12 (2H, s, —$CH_2$—Ar), 7.18~9.04 (12H, m, Ar)

EXAMPLE 63

2,4-bis-(3-dimethylaminobenzylthio)-5,5-dimethyl-5H-imidazole

Initially, 3.1 g of 3-dimethylaminobenzylchloride hydrochloride was added to a mixture of 0.8 g of 5,5-dimethyl-2,4-dithiohydantoin and 1.34 g of sodium methoxide in 50 mL of methanol (MeOH). The reaction mixture was treated following the procedure used in Example 56, and purified by column chromatograph ($CHCl_3$) to give the desired compound in the form of a syrup. The yield of this compound was 1.65 g with a yield ratio of 82.9%.

A comparison of this compound with the compound in Example 61 confirmed identical physical data such as identical $^1$H-NMR analysis data of these two compounds, which indicated that these two compounds are identical with each other.

EXAMPLE 64

2,4-bis-(4-dimethylaminobenzylthio)-5,5-dimethyl-5H-imidazole

Initially, 3.2 g of 4-dimethylaminobenzylchloride hydrochloride was added to a solution of 1 g of 5,5-dimethyl-2,4-dithiohydantoin in 50 mL of ethanol (EtOH). The reaction mixture was treated following the procedure used in Example 62, and purified by column chromatography ($CHCl_3$). Recrystallization form diethyl ether-n-hexane gave the desired compound in the form of a needle-like crystal. The yield of this compound was 1.9 g with a yield ratio of 71.2%, and the melting point was 91°–92° C.

A result of a $^1$H-NMR analysis of the compound is as follows:

$^1$H-NMR ($CDCl_3$, δ, ppm, TMS) 1.33 (6H, s, —$CH_3$×2), 2.89 {12H, s, —N($CH_3$)$_2$33 2}, 4.34 (2H, s, —$CH_2$—Ar), 4.36 (2H, s, —$CH_2$—Ar), 6.91~7.54 (8H, m, Ar)

EXAMPLE 65

2-(2-dimethylaminobenzylthio)-4-benzylthio-5,5-dimethyl-5H-imidazole

To a solution of 1 g of 2-(2-dimethylaminobenzylthio)-5,5-dimethylimidazoline-4-one in 30 mL of N,N-dimethylformamide, 60% sodium hydride in mineral oil (0.15 g) was added at −10° C. After the mixture was stirred for 15 minutes, there was added 0.43 mL of benzylbromide. The reaction mixture was treated following the procedure used in Example 35. The desired compound was obtained as in powder form. The yield of this compound was 0.98 g with a yield ratio of 77.4%.

A result of a $^1$H-NMR analysis of the compound is as follows:

$^1$H-NMR ($CDCl_3$, δ, ppm, TMS) 1.37 (6H, s, —$CH_3$×2), 2.73 {6H, s, —N($CH_3$)$_2$}, 4.47 (2H, s, —$CH_2$—Ar), 4.60 (2H, s, —$CH_2$—Ar), 6.93~7.70 (9H, m, Ar)

EXAMPLE 66

2-benzylthio-4-(2-dimethylaminobenzylthio)-5,5-dimethyl-5H-imidazole (1) Initially, 1.91 mL of benzylbromide was added to a solution of 1.6 g of 5,5-dimethyl-2,4-dithiohydantoin in 50 mL of ethanol (EtOH). The reaction mixture was stirred at the room temperature for one hour, and concentrated in vacuo. The residue was treated following the procedure used in Example 62, and purified by column chromatography ($CHCl_3$). Recrystallization from diethyl ether-n-hexane gave 2-benzylthio-5,5-dimethylimidazolin-4-thione in the form of a needle-like crystal. The yield of this compound was 0.87 g with a yield ratio of 34.8%, and the melting point was 133°–134° C.

A result of a $^1$H-NMR analysis of the compound is as follows:

$^1$H-NMR ($CDCl_3$, δ, ppm, TMS) 1.40 (6H, s, —$CH_3$×2), 4.58 (2H, s, —$CH_2$—Ar), 7.23~7.73 (5H, m, Ar)

(2) Initially, 0.65 g of 2-dimethylaminobenzylchloride hydrochloride was added to a solution of 0.7 g of 2-benzylthio-5,5-dimethylimidazolin-4-thione in 20 mL of ethanol (EtOH). The reaction mixture was stirred at the room temperature for one hour, and concentrated in vacuo. The residue was treated following the procedure used in Example 62, and purified by column chromatography ($CHCl_3$). Recrystallization from diethyl ether-n-hexane gave 2-benzylthio-4-(2-dimethylaminobenzylthio)-5,5-dimethyl-5H-imidazole in the form of a needle-like crystal. The yield of this compound was 0.75 g with a yield ratio of 72.2%, and the melting point was 91°–92° C.

A result of a $^1$H-NMR analysis of the compound is as follows:

¹H-NMR (CDCl₃, δ, ppm, TMS) 1.36 (6H, s, —CH₃×2), 2.69 {6H, s, —N(CH₃)₂}, 4.41 (2H, s, —CH₂—Ar), 4.61 (2H, s, —CH₂—Ar), 6.87~7.58 (9H, m, Ar)

EXAMPLE 67

1-N-methyl-2-(2-dimethylaminobenzylthio)-4,4-dimethyl-2-imidazolin-5-thione

Initially, 5 g of 2-dimethylaminobenzylchloride hydrochloride was added to a solution of 4 g of 3,5,6-trimethyl-2,4-dithiohydantoin in 150 mL of chloroform (CHCl₃) at 60° C. The reaction mixture was stirred for 15 minutes and washed with an aqueous solution of NaHCO₃, dried over MGSO₄ and concentrated in vacuo. The residue was chromatographed on a column of silica gel [(ethyl acetate:n-hexane=1:50 (v/v)]. After removal of the solvent, the desired compound was crystallized. The yield of this compound was 5.32 g with a yield ratio of 75.4%, and the melting point was 76°–78° C.

A result of a ¹H-NMR analysis of the compound is as follows:

¹H-NMR (CDCl₃, δ, ppm, TMS) 1.43 (6H, s, —CH₃×2), 2.70 {6H, s, —N(CH₃)₂}, 3.33 (3H, s, N—CH₃), 4.60 (2H, s, —CH₂—Ar), 7.00~7.70 (4H, m, Ar)

EXAMPLE 68

Inhibitory effect on water-immersion restraint stress-induced gastric ulcer

Male 7-week SD rats were fasted for 24 hours, with a fast of water beginning in early morning of the day when the experiments were performed. The rats were classified into groups each consisting of five rats, such that all the groups have substantially the same average weight. Before giving a stress to the rats, the compounds of the Examples indicated in TABLE 1 were orally administered as specimen drugs to the rats, with a dose of 10 mg/kg. The rats were then kept in stress cages, and were given a stress by immersing the cages in a water bath kept at a substantially constant temperature of 23°±1° C., such that the water level was at the height of the xiphoid of the rats. Seven hours later, the specimen rats were sacrificed by ether, and the mucosa of the stomach of each rat was semi-fixed with 2% formalin. The longitudinal length of the damaged area of the gastric mucosa was measured. A sum of the measured length values of the rats of each group was calculated as an ulcer index. An anti-ulcer or ulcer inhibitory percent (%) was calculated as {1−(ulcer index of each group of specimen rats)/(ulcer index of non-specimen group)}×100. The ulcer inhibitory percent values corresponding to the individual specimen drugs are indicated in TABLE 1.

TABLE 1

| Drug (Examples) | Dose (mg/kg) | Inhibitory Percent (%) |
| --- | --- | --- |
| 4 | 10 | 63.3 |
| 5 | 10 | 23.3 |
| 13 | 10 | 46.3 |
| 16 | 10 | 82.4 |
| 18 | 10 | 34.1 |
| 22 | 10 | 48.9 |
| 28 | 10 | 73.8 |
| 35 | 10 | 30.6 |
| 44 | 10 | 28.8 |

EXAMPLE 69

Inhibitory effect on hydrochloric acid.ethanol-induced gastric ulcer

Male SD rats of 7-week age were fasted for 24 hours, with a fast of water beginning in early morning of the day when the experiments were performed. The rats were classified into groups each consisting of five rats, such that all the groups have substantially the same average weight. Before giving hydrochloric acid.ethanol to the rats, the compounds of the Examples indicated in TABLE 2 were orally administered as specimen drugs to the rats, with a dose of 30 mg/kg. Thirty minutes later, 1 mL of 98% ethanol containing 200 mM of hydrochloric acid was orally administered to each specimen rat. One hour later, the specimen rats were sacrificed by ether, and the mucosa of the stomach of each rat was semi-fixed with 2% formalin. The longitudinal length of the damaged area of the gastric mucosa was measured, and the anti-ulcer percent values of the individual specimen drugs were calculated on the basis of the sum of the measured length values of each group of the specimen rats, in the same manner as in Example 68. The calculated ulcer inhibitory percent values are indicated in TABLE 2.

TABLE 2

| Drug (Examples) | Dose (mg/kg) | Inhibitory Percent (%) |
| --- | --- | --- |
| 1 | 30 | 71.9 |
| 8 | 30 | 93.0 |
| 9 | 30 | 94.9 |
| 18 | 30 | 37.4 |
| 21 | 30 | 99.6 |
| 23 | 30 | 83.6 |
| 29 | 30 | 69.5 |
| 34 | 30 | 52.0 |
| 41 | 30 | 74.5 |

EXAMPLE 70

Healing effect on acetic acid-induced gastric ulcer of rat

A male Donryu rat of 7-week age was subjected to abdominal incision to expose the stomach, with pentobarbital used as an anesthesia. Using a metal ring having an inside diameter of 10 mm, 200 µL of glacial acetic acid was applied for contact with a serosa-side part of a boundary area between the antrum and the corpus body. The abdomen of the specimen rat subjected to the glacial acetic acid was closed by an operation, and the rat was then fed in a normal way. The compound obtained in Example 16 was orally administered as a specimen drug to the specimen rat two times a day (at 9:00 a.m. and 5:00 p.m.), each time with a dose of 50 mg/kg, beginning on the day following the day on which the glacial acetic acid was applied to the rat. The oral administration continued for 10 consecutive days, with a total of 20 administrations. On the day following the last day of administration, the specimen rat was sacrificed with ether, and the ulcer portion of the rat was fixed with formalin. The surface area of the ulcer portion was measured. The healing percent (%) calculated on the basis of the measured surface area was 28.9%.

It will be understood from the results of the tests in Examples 68–70 that the compounds according to the present invention exhibited excellent effects of promoting the curing of ulcers.

EXAMPLE 71

Single-dose toxicity study

Ten male ddY mice (each having a weight of 22–28 g) were used as specimen animal in a cage kept at a substantially constant temperature of 23°±1° C. and under a substantially constant humidity of 55±5%. The compound prepared in Example 39, that is, 2-(2-dimethylaminobenzylthio)-5,5-dimethylimidazolin-4-thione was used as the specimen drug. This compound was suspended in a 2% solution of polysorbate 80, and the suspension was administered to each specimen mouse, with different doses. The specimen mice were observed for two weeks after the administration. On the basis of the death percent, lethal dose ($LD_{50}$) which causes a 50% death was obtained as an index indicative of the single dose toxicity. The obtained median lethal dose $LD_{50}$ (oral administration) was 2000 mg/kg or more. It was thus confirmed that the median lethal dose $LD_{50}$ (oral administration) of the compound according to the present invention was sufficiently large, indicating a low degree of toxicity or a high degree of safety.

Referring to the following Examples, there will be illustrated some examples of anti-ulcer drugs, which are prepared from the compounds according to the present invention, in various known manners, in various forms which include those illustrated below.

EXAMPLE 72

Anti-ulcer drug (tablet)

The drug is prepared in an ordinary manner such that each tablet (200 mg) contains the following components:

Effective component 30 mg (Compound in each Example)
Lactose 103 mg
Corn starch 50 mg
Magnesium stearate 2 mg
Hydroxypropyl cellulose 15 mg

EXAMPLE 73

Anti-ulcer drug (capsule)

The drug is prepared in an ordinary manner such that each gelatin capsule (340 mg) contains the following components:

Effective component 30 mg (Compound in each Example)
Lactose 200 mg
Corn starch 70 mg
Polyvinylpyrrolidone 5 mg
Crystalline cellulose 35 mg

EXAMPLE 74

Anti-ulcer drug (granule)

The drug is prepared in an ordinary manner such that 1 g of granule contains the following components:

Effective component 100 mg (Compound in each Example)
Lactose 550 mg
Corn starch 300 mg
Hydroxypropyl cellulose 50 mg It will be understood that the imidazole derivative as represented by the above formulas (44) is a novel compound which is effective to cure or remedy gastric ulcers, being capable of exhibiting excellent anti-ulcer effects of inhibiting or suppressing the aggressive factors and promoting or intensifying the protective factors. According to the process of producing the imidazole derivative, the novel compound having excellent anti-ulcer effects as indicated above can be advantageously produced. The present compound having such excellent anti-ulcer effects may be used as an effective component of an anti-ulcer drug effective to cure the gastric ulcers.

We claim:

1. An imidazole derivative or pharmaceutically acceptable salt thereof, which is represented by one of the following formulae (1-1) through (1-4),

wherein $R_1$ and $R_2$ represent a same one or respective different ones of a hydrogen atom, a lower alkyl group, a phenyl group, and a benzyl group, or in combination represent one of an alkylene group having 2–6 carbon atoms, an alkylidene group having 2–5 carbon atoms and a benzylidene or cinnamylidene group, while $R_3$ represents one of a hydrogen atom, a lower alkyl group, a benzyl group, a lower alkanoyl group and a benzoyl group, and wherein at least one of A and X represents a group represented by the following formula (2),

wherein m represents an integer from 1 to 4, and $R_4$ represents a phenyl group represented by the following formula (3),

wherein $R_5$ and $R_6$ represent a same one or respective different ones of a hydrogen atom, a lower alkyl group, a lower alkenyl group, a lower alkanoyl group, a lower alkanoyl group substituted with a halogen atom, a benzoyl group or a benzoyl group substituted with a halogen atom, while $R_7$ represents one of a hydrogen atom, a halogen atom, a hydroxyl group, a lower alkyl group, a lower alkoxy group and a nitro group, and wherein the other of A and X represents one of an oxygen atom, a sulfur atom, a hydroxyl group, a mercapto group, a group represented by said formula (2), an alkylthio group, an alkenylthio group, and a benzylthio group, and the broken line in said formulae (1-1), (1-2) and (1-3) represents a bond effective only when an appropriate one of A and X represents the oxygen or sulfur atom.

2. An imidazole derivative or pharmaceutically acceptable salt thereof according to claim 1, wherein $R_1$ and $R_2$ represent a same one or respective different ones of a hydrogen atom, an alkyl group having 1–7 carbon atoms and a phenyl group, or in combination represent one of an alkylidene group having 2–5 carbon atoms, a benzylidene or cinnamylidene group, and an alkylene group having 2–6 carbon atoms, $R_3$ representing one of a hydrogen atom, an alkyl group having 1–7 carbon atoms, an alkanoyl group having 2–5 carbon atoms, a benzoyl group, and a benzyl or cinnamyl group, and wherein at least one of A and X represents one of a group represented by said formula (2), while the other of said A and X represents one of an oxygen atom, a sulfur atom, a hydroxyl group, a mercapto group, an alkylthio group having 1–7 carbon atoms, an alkenylthio group, a benzylthio group, a cinnamylthio group, and a group represented by said formula (2), $R_4$ in said formula (2) representing one of an alkyl group having 1–4 carbon atoms, an alkoxy group, and a group represented by said formula (3), $R_5$ and $R_6$ in said formula (3) representing a same one or respective different ones of a hydrogen atom, an alkyl group having 1–5 carbon atoms, an alkenyl group having 1–5 carbon atoms, an alkanoyl group of 1–5 carbon atoms, a benzoyl group or a benzoyl group substituted with a halogen atom, $R_7$ representing one of a hydrogen atom, a hydroxyl group, a halogen atom, an alkyl group having 1–5 carbon atoms, an alkoxy group having 1–5 carbon atoms and a nitro group.

3. An imidazole derivative or pharmaceutically acceptable salt thereof, which is represented by one of the following formulae (4-1), (4-2) and (4-3),

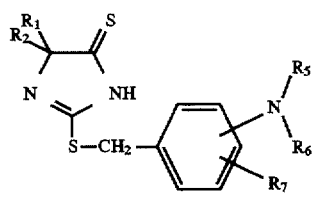
(4-1)

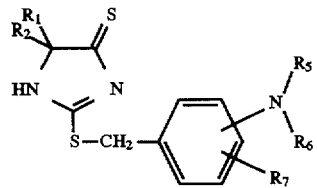
(4-2)

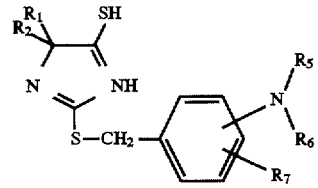
(4-3)

wherein $R_1$ and $R_2$ represent a same or respective ones of a hydrogen atom, an alkyl group having 1–7 carbon atoms, and a phenyl group or in combination represent one of an alkylidene group having 2–5 carbon atoms, a benzylidene or cinnamylidene group, and an alkylene group having 2–6 carbon atoms, $R_5$ and $R_6$ representing a same one or respective different ones of a hydrogen atom, an alkyl group having 1–5 carbon atoms, an alkenyl group having 1–5 carbon atoms, an alkanoyl group of 1–5 carbon atoms, a benzoyl group or a benzoyl group substituted with a halogen atom, $R_7$ representing one of a hydrogen atom, a hydroxyl group, a halogen atom, an alkyl group having 1–5 carbon atoms, an alkoxy group having 1–5 carbon atoms and a nitro group.

4. An imidazole derivative or pharmaceutically acceptable salt thereof, which is represented by the following formula (5),

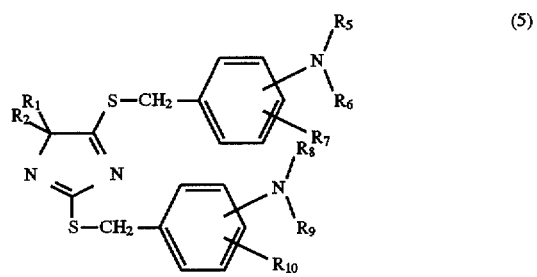
(5)

wherein $R_1$ and $R_2$ represent a same or respective ones of a hydrogen atom, an alkyl group having 1–7 carbon atoms, and a phenyl group, or in combination represent one of an alkylidene group having 2–5 carbon atoms, a benzylidene or cinnamylidene group and an alkylene group having 2–6 carbon atoms, $R_5$, $R_6$, $R_8$ and $R_9$ representing a same one or respective different ones of a hydrogen atom, an alkyl group having 1–5 carbon atoms, an alkenyl group having 1–5 carbon atoms, an alkanoyl group of 1–5 carbon atoms, a benzoyl group or a benzoyl group substituted with a halogen atom, $R_7$ and $R_{10}$ each representing any one of a hydrogen atom, a hydroxyl group, a halogen atom, an alkyl group having 1–5 carbon atoms, an alkoxy group having 1–5 carbon atoms and a nitro group.

5. A composition for treating ulcers comprising an anti-ulcer effective amount of an imidazole derivative or pharmaceutically acceptable salt thereof, said imidazole derivative or said salt being represented by one of the following formulae (41-1) through (41-4),

(41-1)

(41-2)

(41-3)

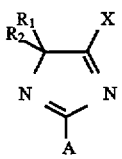

(41-4)

wherein $R_1$ and $R_2$ represent a same one or respective different ones of a hydrogen atom, a lower alkyl group, a phenyl group, and a benzoyl group, or in combination represent one of an alkylene group having 2–6 carbon atoms, an alkylidene group having 2–5 carbon atoms or a benzoylidene or cinnamylidene group, while $R_3$ represents one of a hydrogen atom, a lower alkyl group, a benzyl group, a lower alkanoyl group and a benzoyl group, and wherein at least one of A and X represents a group represented by the following formula (42),

wherein m represents an integer from 1 to 4, and $R_4$ represents a phenyl group represented by the following formula (43),

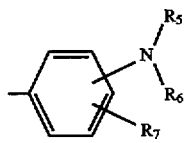

(43)

wherein $R_5$ and $R_6$ represent a same one or respective different ones of a hydrogen atom, a lower alkyl group, a lower alkenyl group, a lower alkanoyl group, a lower alkanoyl group substituted with a halogen atom, a benzoyl group, or a benzoyl group substituted with a halogen atom, while $R_7$ represents one of a hydrogen atom, a halogen atom, a hydroxyl group, a lower alkyl group, a lower alkoxy group and a nitro group, and wherein the other of A and X represents one of an oxygen atom, a sulfur atom, a hydroxyl group, a mercapto group, a group represented by said formula (42), an alkylthio group, alkenylthio group, and a benzylthio group, and the broken line in said formula (41-1), (41-2) and (41-3) represents a bond effective only when an appropriate one of A and X represents the oxygen or sulfur atom and a carrier therefor.

6. The imidazole derivative or pharmaceutically salt thereof of claim 3, wherein one of the formulas (4-1) and (4-2) represents 2-(2-dimethylaminobenzylthio)-5,5-dimethylimidazolin-4-thione.

7. The imidazole derivative or pharmaceutically acceptable salt thereof of claim 3, wherein one of the formulas (4-1) and (4-2) represents 2-(2-N-isobutyl-N-methylaminobenzylthio)-5,5-dimethylimidazolin-4-thione.

8. The imidazole derivative or pharmaceutically acceptable salt thereof of claim 3, wherein one of the formulas (4-1) and (4-2) represents 2-(2-N-trifluoroacetylaminobenzylthio)-5,5-dimethylimidazolin-4-thione.

9. The imidazole derivative or pharmaceutically acceptable salt thereof of claim 3, wherein one of the formulas (4-1) and (4-2) represents 2-(2-aminobenzylthio)-5,5-dimethylimidazolin-4-thione.

10. The composition of claim 5, wherein said imidazole derivative is 2-(2-dimethylaminobenzylthio)-5,5-dimethylimidazoline-4-thione.

11. The composition of claim 5, wherein said imidazole derivative is 2-(2-N-isobutyl-N-methylaminobenzylthio)-5,5-dimethylimidazolin-4-thione.

12. The composition of claim 5, wherein said imidazole derivative is 2-(2-N-trifluoroacetylaminobenzylthio)-5,5-dimethylimidazolin-4-thione.

13. The composition of claim 5, wherein said imidazole derivative is 2-(2-aminobenzylthio)-5,5-dimethylimidazolin-4-thione.

\* \* \* \* \*